United States Patent [19]

Netzer

[11] Patent Number: 5,801,307

[45] Date of Patent: Sep. 1, 1998

[54] DIFFERENTIAL WINDSHIELD CAPACITIVE MOISTURE SENSORS

[76] Inventor: Yishay Netzer, Yuvalim, Doar Na Misgav, Israel

[21] Appl. No.: 782,194

[22] Filed: Jan. 10, 1997

Related U.S. Application Data

[63] Continuation-in-part of Ser. No. 501,684, Jul. 12, 1995, Pat. No. 5,682,788.

[51] Int. Cl.[6] .................................................. G01N 1/00
[52] U.S. Cl. ............................................... 73/170.17
[58] Field of Search ........................... 73/335.05, 170.17; 324/61, 671

[56] References Cited

U.S. PATENT DOCUMENTS

| | | | |
|---|---|---|---|
| 3,826,979 | 7/1974 | Steinmann | 324/61 R |
| 3,902,040 | 8/1975 | Ikeda et al. | 219/203 |
| 4,567,412 | 1/1986 | Graham | 318/483 |
| 4,797,605 | 1/1989 | Palanisamy | 324/65 R |
| 4,805,070 | 2/1989 | Koontz et al. | 361/286 |
| 4,987,354 | 1/1991 | Steinmann | 318/444 |
| 5,040,411 | 8/1991 | Medzious | 73/73 |
| 5,223,796 | 6/1993 | Waldman et al. | 324/687 |
| 5,402,075 | 3/1995 | Lu et al. | 324/664 |
| 5,551,288 | 9/1996 | Geraldi et al. | 73/170.26 |

Primary Examiner—Hezron E. Williams
Assistant Examiner—Jay Politzer
Attorney, Agent, or Firm—Mark M. Friedman

[57] ABSTRACT

A differential capacitive moisture sensor, relying for its operation on the time-varying couplings in two moisture-sensing regions to provide indication of presence of moisture, with selectivity of sensing surface provided by a shielding electrode, and with temperature information provided by a simultaneously-fabricated resistive temperature sensor. Various electrode connections and sensor electronics may be used. An improved differential capacitive moisture sensor has equal dry capacitances, with unequal moisture sensitivities, for providing a single-polarity output signal. An ice detection method and apparatus is also provided.

12 Claims, 21 Drawing Sheets

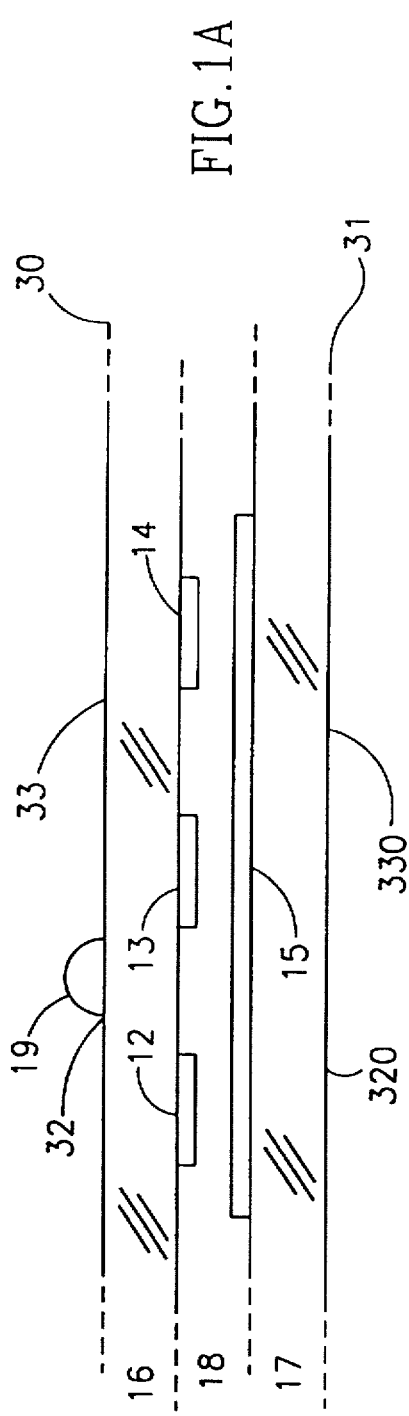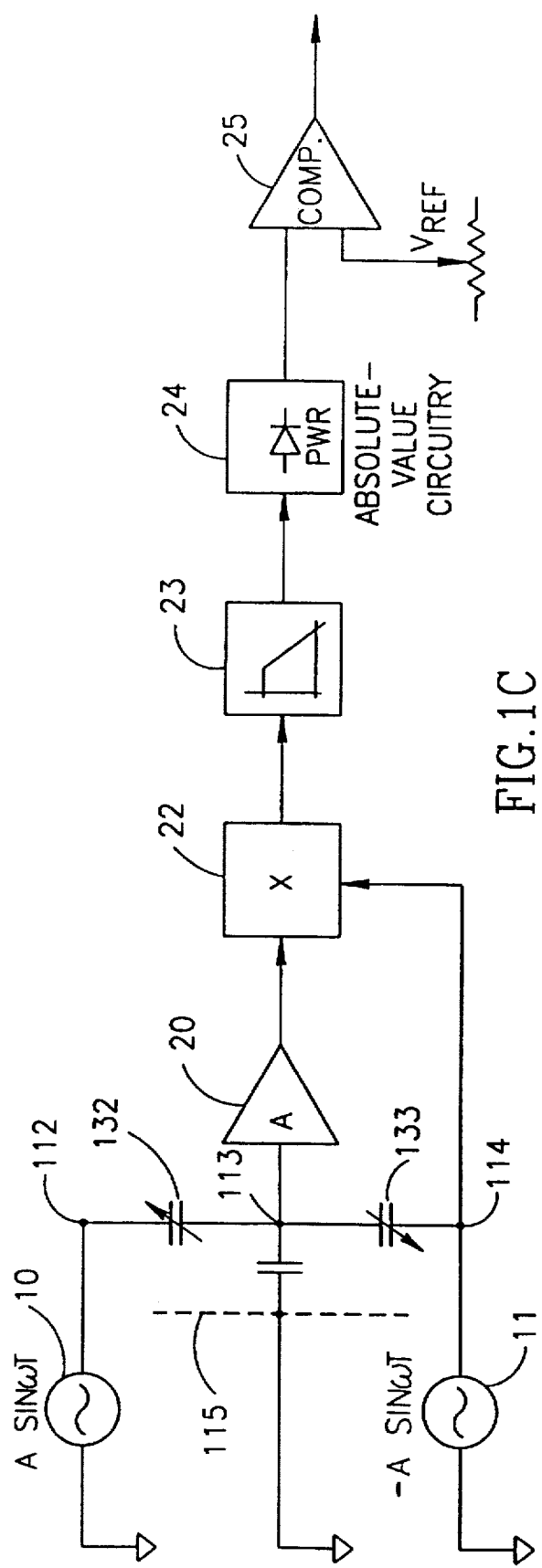

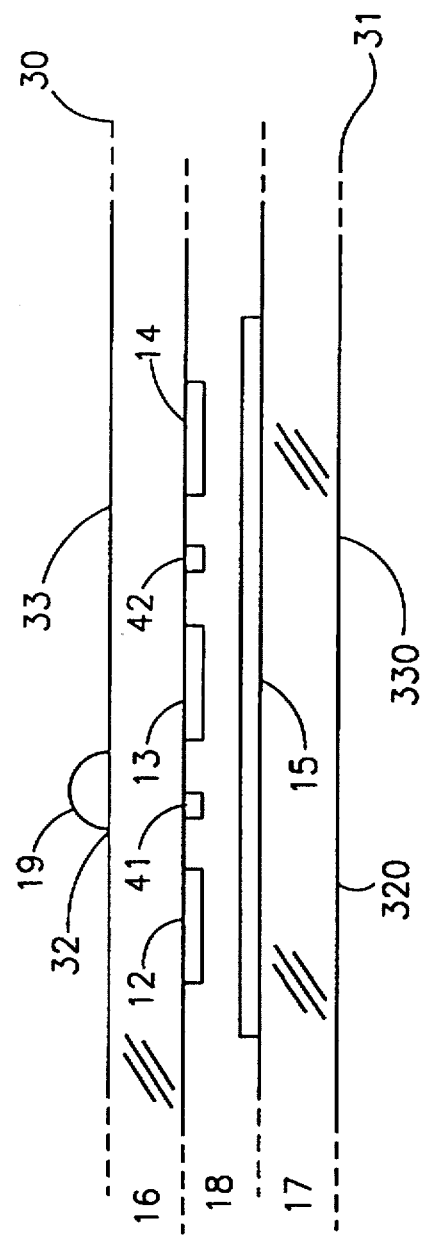

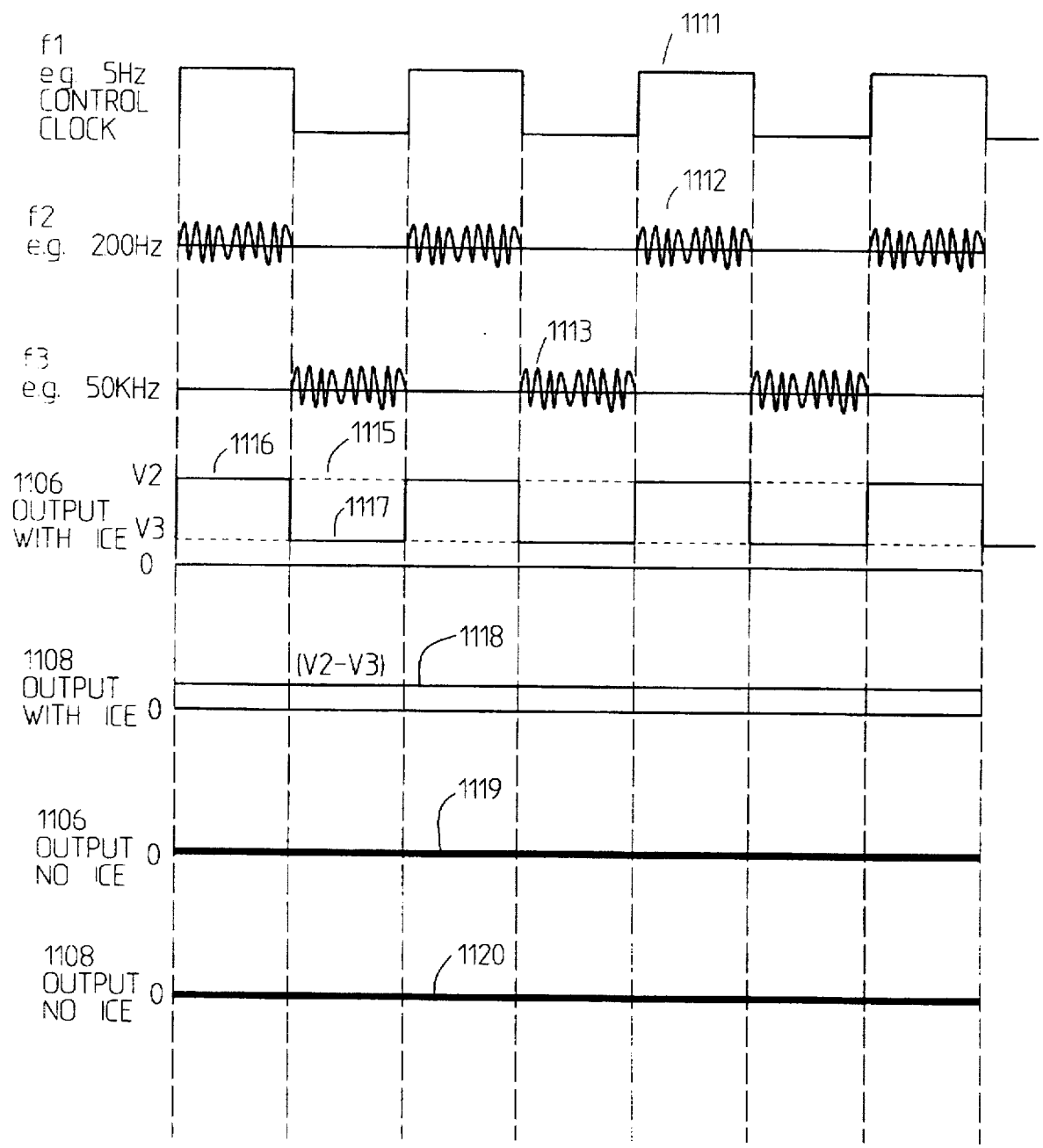

DIFFERENTIAL WINDSHIELD CAPACITIVE MOISTURE SENSORS

This is a CIP of application Ser. No. 08/501,684, filed 12 Jul. 1995 allowed 5,682,788.

FIELD AND BACKGROUND OF THE INVENTION

The present invention relates to a moisture sensor and, more particularly to a moisture sensor especially suitable for use in the sensing of moisture on an automobile windshield. This device operates on a differential capacitive moisture detection principle, which has been discovered by the inventor, and will be described below, which results in a sensor with greater sensitivity, and additionally, with water-directionality, the ability to selectively sense moisture on either surface of the windshield, a feature not found in the prior art. Prior Art automotive windshield moisture sensors are either bulky, conspicuous, expensive, electro-optical moisture sensors, of limited sensing area, simultaneously expensive, and having mounting position limitations; or, capacitive moisture sensors, which are unable to distinguish between a moisture signal and normally-encountered background reference signal variations due to stress and temperature variations in the dimensions of the windshield.

Various attempts have been made to solve the specific problems of the electro-optical moisture sensors, as mentioned above. These have been in the category of single-ended capacitive moisture sensors, which operate by providing changes in electrical capacitance between two sensing electrodes, in response to presence of moisture on a surface in the region between the electrodes. These have the aforementioned difficulty of distinguishing between baseline signal and moisture signal, as mentioned above, due to the large "dry-" condition background baseline signal, and small change to this signal level due to presence of rain. Therefore, variations of output which indicate rain are comparable to normally-encountered changes in baseline reference signal, giving false indications, and non-indications, concerning presence of moisture. A further disadvantage of prior-art capacitive moisture sensors is the inability to distinguish between moisture on the outside versus on the inside of the windshield, making it difficult to use as a wiper controller or as a defogger or as a defroster sensor. For these reasons, the capacitive moisture sensors are not practical, and do not appear to be presently in wide use in the automotive marketplace.

In more detail, in the prior art, electro-optical moisture sensors are the most common and are used for detection of raindrops by sensing of change in the total internal reflection of light beams off the front windshield glass-air interface. A typical sensor of this type is described in U.S. Pat. No. 4,859,867. Electro-optical moisture sensors suffer from several disadvantages:

They are conspicuously mounted on the internal side of the windshield.

The proper operation is critically dependent on the mechanical stability of the mounting.

They are often sensitive to extraneous light.

They are relatively expensive.

An alternative method of sensing moisture on the windshield surface relies on the relatively large dielectric constant electrodes of water (approximately 80) as it affects the capacitance between a set of conductive transparent electrodes deposited on the windshield. Sensors based on this method are integral with the windshield and are potentially less expensive and non-conspicuous. Two such sensors are described in U.S. Pat. Nos. 4,805,070 and #4,831,493. In these patents, a conductive coating is applied on the outside surface of the windshield. Its disadvantage is exposure to abrasion due to the combined effects of wiper motion and airborne particles. Another approach is to deposit the conductive electrodes on the inside of the front laminate of the "sandwich" windshield glass for protection of the conductive coating. Typical moisture sensors of this type are described in U.S. Pat. No. 4,703,237; in U.S. Pat. No. 4,827,198; in U.S. Pat. No. 4,613,802; and in U.S. Pat. No. 4,554,493; where the capacitive effect of water drops changes the resonant frequency of a resonant circuit. In all prior art capacitive moisture sensors in which the dielectric glass layer separates the capacitor plates from the water-droplets-sensitive surface, the relative change of the capacitance due to water drops is very small. The capacitive moisture sensor described in U.S. Pat. No. 3,826,979 aims to diminish the fixed constituent of the capacitance (in the dry condition) by shielding part of the parasitic capacitive coupling, thereby reducing the dry reference background signal level. The improvement, however, is only partial since the residual "dry" capacitance is still significant relative to the moisture induced capacitance increase. A further difficulty is that the "dry" capacitance itself is not stable, in particular as a result of distortion in the internal plastic layer—that result from windshield dimensional changes due to temperature and mechanically induced stress. As a result, the signal due to surface moisture is virtually indistinguishable from the error signal due to capacitance changes. The reliability of this kind of capacitive windshield moisture sensors is therefore poor.

An additional shortcoming of prior art capacitive moisture sensors is their non-directionality, i.e., their sensitivity to moisture on both surfaces of the windshield, i.e., they do not distinguish between moisture on the external surface of the windshield and condensation on the internal side. Similarly, they are sensitive to adjacent objects in the inside of the car, such as when the driver manually wipes off condensation accumulated on the internal surface.

Thus, in general, capacitive windshield moisture sensors suffer from both lack of sensitivity and stability on the one hand, and from non-directionality on the other hand. For this reason only electro-optical windshield rain sensors have had any commercial success.

There is thus a widely recognized need for, and it would be highly advantageous to have, an improved moisture sensor, suitable for automotive windshield application, which is inexpensive, sensitive, stable with time and temperature, does not obstruct the driver's view so it is flexible with respect to mounting position, and is "directional", i.e., it is selectively sensitive to moisture on only one side of the windshield.

SUMMARY OF THE INVENTION

According to the present invention there is provided an automotive windshield moisture sensor.

According to further features in preferred embodiments of the invention described below, there is provided a directional windshield moisture sensor.

According to another embodiment, there is provided a pair of directional moisture sensors, integrally manufactured in the windshield structure.

According to another embodiment, there is provided an additional temperature sensor element, which, in conjunction with the moisture sensor, provides the capability to differentiate snow or ice from rain or "fogging" condensation such as often found on the inside of the windshield.

According to another embodiment, the moisture detector is simultaneously, integrally, manufactured in the windshield with an electrical heating layer in the windshield.

According to another embodiment there is provided an independent moisture detector, which can be separately manufactured, and which is suitable for mounting on a conventional windshield.

The present invention successfully addresses the shortcomings of the presently known configurations by providing capacitive moisture sensor.

The present invention discloses a novel, directional, differential, capacitive moisture sensor, which solves the problems of automotive windshield moisture-sensing.

More specifically, the directional, differential, capacitive moisture sensor of the present invention, is inexpensive, does not obstruct the drivers view, can be placed in the wiping area, is not subject to aging due to abrasion, is sensitive, and stable with time and with stress and temperature effects on windshield dimensions, is sensitive to moisture on only one surface of the windshield, hence insensitive to moisture and conductive objects on or near the opposite surface of the windshield. Also, this moisture sensor is capable of sensing moisture over a large surface area, unlike the electro-optical moisture detectors, which are focussed to sample moisture only in a small region.

One "unit" of the moisture sensor of the invention may be "mounted", either as a separately manufactured add-on device, or integrally manufactured, in a windshield, for the purpose of rain-sensing, by monitoring moisture on the outer surface of the windshield. Incorporating a temperature-sensor, as mentioned above, then gives the capability to differentiate between non-freezing rain, and freezing precipitation, snow, slush, ice, freezing rain, necessitating windshield heating, as well as wiping. A second unit may be "mounted" in the opposite orientation, to control a blower or blower-plus-heater, to "defog" or "defrost" the inner windshield surface, again, preferably in conjunction with a temperature sensor to control the temperature of the air source provided to the blower, as appropriate to the moisture to be dissipated. A pair of moisture sensors may be integrally manufactured with the windshield, temperature-sensor, and heating element; or add-on unit may be provided in existing cars as an after-market product.

An improved differential capacitive moisture sensor has equal dry capacitances, with unequal moisture sensitivities, for providing a single-polarity output signal.

Yet further, it is an object of the present invention to provide a method and apparatus for differentiating between solid-state water (ice) and liquid-state water.

BRIEF DESCRIPTION OF THE DRAWINGS

The invention is herein described, by way of example only, with reference to the accompanying drawings, wherein:

FIG. 1A is a directional, differential, capacitive moisture sensor;

FIG. 1C is a schematic of the sensor of FIG. 1A, 1B;

FIG. 3A is another modification of the sensor of FIG. 1A;

FIG. 11C illustrates signals in the ice detector electronics;

DESCRIPTION OF THE PREFERRED EMBODIMENTS

Figure 1B:
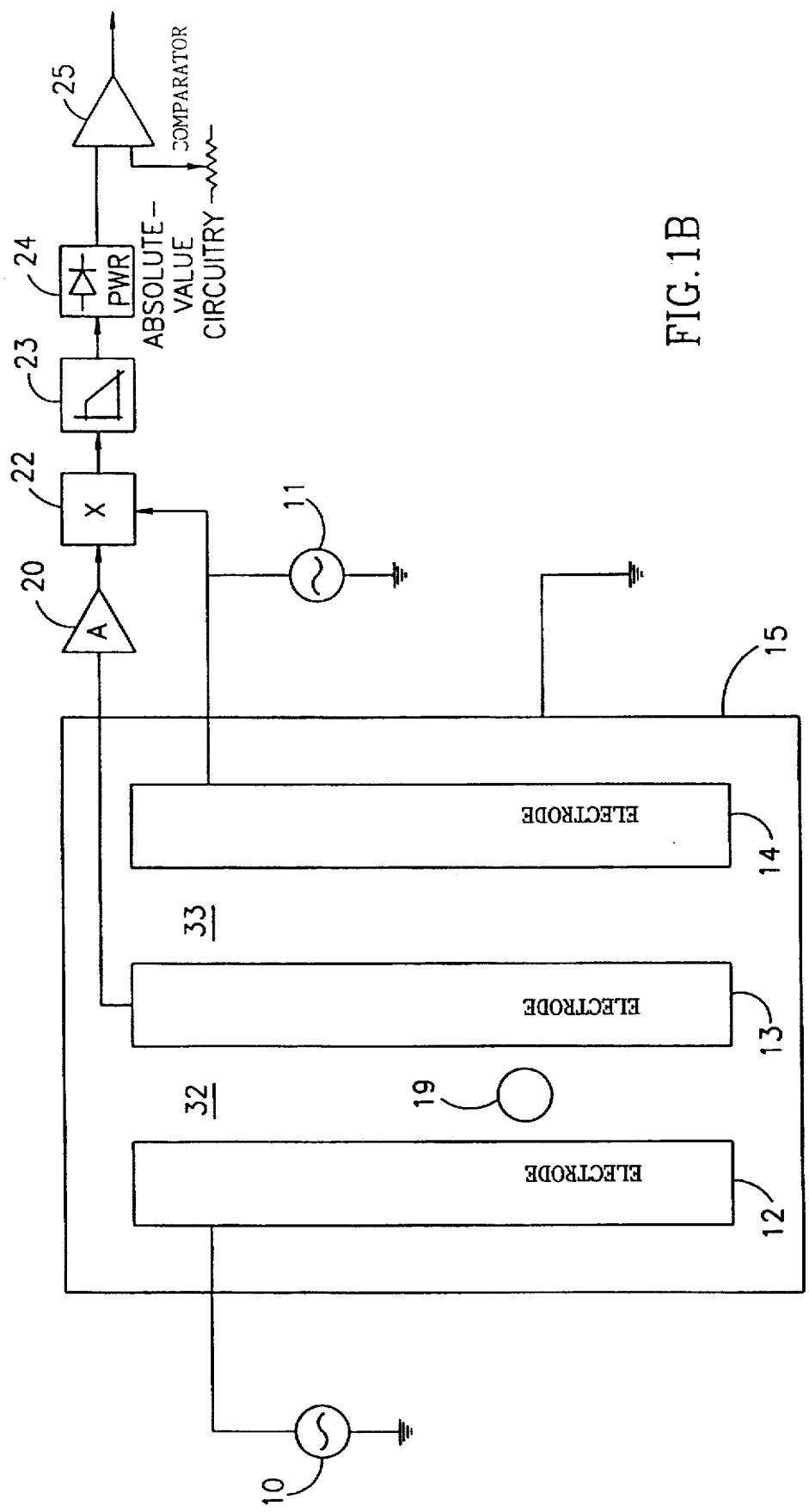
FIG. 1B is the directional, differential, capacitive moisture sensor of FIG. 1A, with one possible configuration of excitation and sensing electronics.

The present invention is of a directional, differential, capacitive moisture sensor, which can be integrally manufactured in an automotive windshield, or as an add-on device.

Specifically, the present invention can be used to sense presence of various types of moisture on a windshield, and to differentiate between them, sufficiently well to control wipers, heater and blower, for wiping, de-icing, defogging and defrosting, to restore, or maintain the drivers visibility.

The principles and operation of a directional, differential, capacitive, moisture sensor according to the present invention may be better understood with reference to the drawings and the accompanying description.

Referring now to the drawings, FIG. 1A illustrates the simplest "unit" directional, differential, capacitive, moisture sensor.

The embodiment in FIG. 1A illustrates the moisture sensor as integrally manufactured in an automotive windshield. The windshield consists of laminated "sandwich glass", two glass laminated layers, 16 and 17, separated by a layer of plastic laminate, 18, with electrodes 12, 13, 14, deposited on the lower surface of glass laminate layer, 16; and electrode, 15, deposited on the upper surface of glass layer, 17. This construction results in a structure such that electrodes on any surface are substantially co-planar with each other, and parallel to all the surfaces of the glass laminates.

For discussion purposes, we will consider the layer, 16, to be the outer layer, and layer 17, to be the inner layer, and we will discuss the effects of moisture on the outer glass laminate surface, 30, and on the inner glass laminate surface, 31. The simplest "unit" moisture sensor of the invention consists of three "active", i.e., non-grounded, electrodes, as will now be described. It is worthwhile to note that the three-electrode Capacitive Detector Device of U.S. Pat. No. 3,826,979, is not in the category of our invention, since its center plate is grounded.

A basic capacitive moisture sensor exhibits capacitance change due to moisture in the sensing area, such as water drop, 19, in sensing area 32 of FIG. 1A. Since water has a dielectric constant of about 80, compared with that of air of about 1, and capacitance of a capacitor is proportional to the dielectric constant of the dielectric between its plates, we see that an increase in moisture in the sensing areas, 32, and 33, between electrode pairs, 12 and 13, and 13 and 14, respectively, will result in an increase in capacitance between the corresponding electrode pairs. If there is uniform increase of moisture in the sensing areas 32 and 33, then the two capacitances will increase equally. If, as in FIG. 1B, balanced, equal frequency and amplitude, 180 degree out-of-phase excitations are applied to the electrodes, 12 and 14, and the spacings are equal, and the sandwich-glass is uniform, then, when both the sensing areas 32 and 33 on surface 30, are dry or uniformly moist, the capacitively coupled signal voltage at electrode 13 due to each, will be identical, and the total will be substantially zero, due to equal coupling, through equal capacitances, independent of the exact capacitance value.

The invention depends on the inventor's realization, that the moisture in the two sensing areas 32 and 33, in general, at any instant of time is not equal, even though the average of the moisture in the two areas over a long period of time may be expected to be equal. Hence, at any given instant, there is an asymmetry in the moisture in the two sensing areas, a corresponding instantaneous capacitance imbalance, a corresponding imbalance of the signal couplings to electrode 13, and a resulting finite, non-zero, detectable, imbalance signal at electrode 13, to indicate presence of moisture. The polarity of the imbalance signal is not known, since which side has greater moisture at any given instant is not known. This is, however, a practical moisture detector, since in the sensing electronics, it is possible to incorporate "absolute-value" circuitry, which then detects imbalance of either polarity.

Because this is a differential sensor, it is substantially insensitive to dimensional changes in the substrate, the laminated windshield sandwich glass, in this example. A stress-induced or temperature induced expansion or contraction is expected to affect the dimensions, especially thickness, of both sensing areas substantially equally, resulting in substantially no false indication of moisture. This feature is due to the differential nature of the sensor, and the substantially uniform dimensional change in the sensing area, and is its first advantage over the prior-art single-ended, non-differential, capacitive moisture sensors.

Further, the differential capacitive moisture sensor is more sensitive to moisture in a practical circuit application than the prior-art single-ended sensors. The single-ended sensors operate with non-zero reference "dry" signal output. Changes in this reference signal must be detected to detect presence of moisture. These changes are small, and the changes due to substrate dimensional changes are of comparable amplitude to the moisture signals, so the prior-art single-ended moisture sensors are not practical. The differential moisture sensor on the other hand has a reference signal of substantially zero, so the moisture signal is immediately large, and easily detected; and the substrate dimensional changes are balanced out, due to sensor symmetry, so there is no error signal due to substrate dimensional changes. For these reasons, the net result is that the differential moisture sensor is much more sensitive than the prior-art single-ended sensors.

Directionality, i.e., sensitivity to moisture on only one surface of the substrate, is provided by the shield electrode, 15, in FIG. 1A. This shield electrode is connected to the electronics system ground, providing electrical isolation of electrode pairs, 12 and 13, and 13 and 14, from regions, 320 and 330, respectively, on surface 31, which would otherwise have also been sensing areas similarly to areas, 32 and 33, respectively, on surface 30. Thus, directionality, sensitivity to moisture on only one surface of the substrate, is provided, as is desirable in the automotive windshield application, as in many other applications for sensors in general.

The flexibility of mounting of the windshield moisture detector is provided by implementing the electrodes as, for example, a vacuum-deposited thin film coating of a transparent, electrically-conductive, material, such as Indium-Tin-Oxide, such as has been used for electrical windshield heating. Using such a transparent material, makes it possible to locate the moisture sensor in the wiping area of the windshield. This is desirable, since wiping will remove the moisture rapidly from the sensed area of the windshield, resulting in de-activation of the wipers promptly upon cessation of rainfall, for example.

When the moisture sensor is used to detect moisture in the form of condensation on the inside of the windshield, the flexibility of mounting is also important, since the automobile designer will want to locate the moisture detector in a position such that after the "defogging" for example, is complete, the blower and heater would be turned off. This depends on the knowledge of the automobile designer of the air flow in the car. It is important to note that this directional, differential, capacitive, windshield, moisture sensor, now makes practical moisture detection on the inside surface of the windshield. Previously, it would have been necessary to mount an electro-optical moisture sensor on the outside of the windshield, to focus it on the inner surface of the windshield.

Figure 4A:
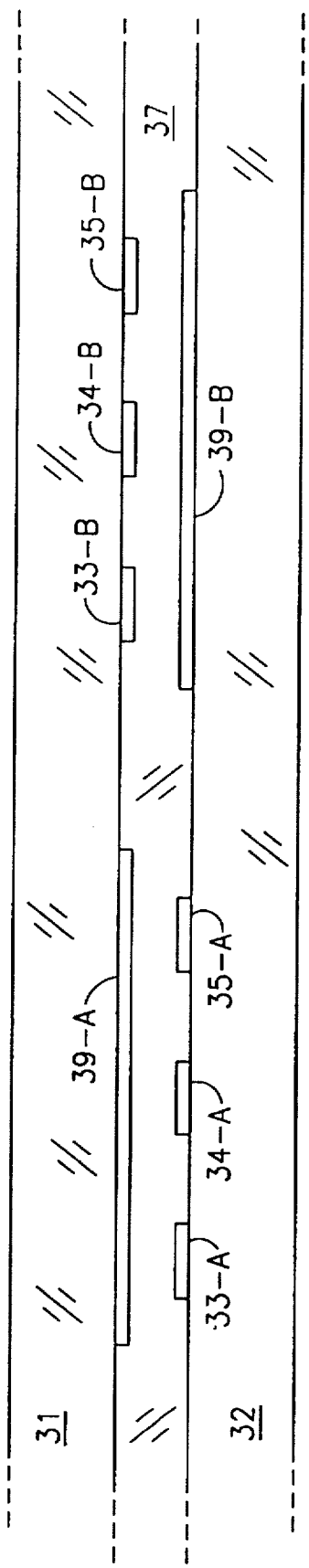
FIG. 4A is a pair of sensors as in FIG. 1A, shown mounted for sensing two surfaces of the windshield.
Figure 4B:
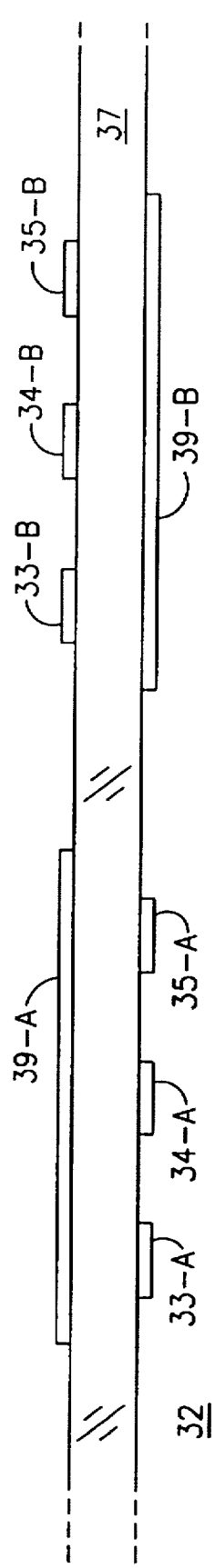
FIG. 4B is a pair of standalone sensors.

A pair of moisture sensors of the invention are shown in FIG. 4A, illustrating the fabrication, to result in one sensor each for moisture on outer and inner windshield surfaces.

Figure 5:
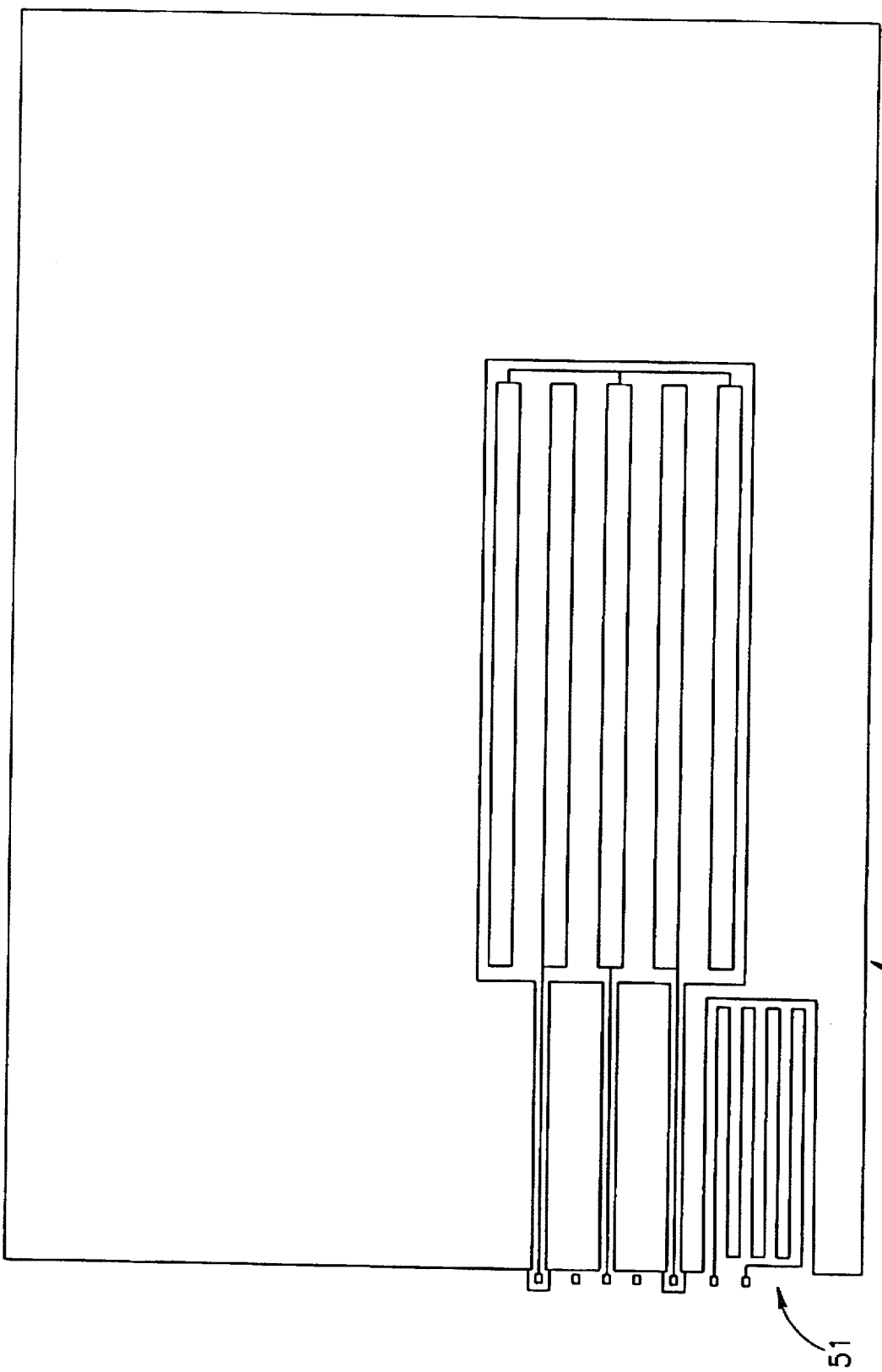
FIG. 5 is an example electrode pattern, incorporating a temperature-sensing element.

As mentioned previously, an accompanying temperature sensor may be implemented with the same vacuum-deposited thin film which is used to fabricate the moisture sensor electrodes. This is conveniently done by depositing as a temperature sensing element, a long, thin, pattern, for example, in the shape of a "snake", element 51, as shown in FIG. 5, accompanying an alternative electrode configuration, which has been built. The resistance of this element as a function of temperature is then monitored.

The electronics for the differential sensor of FIG. 1A are shown in FIG. 1B. An electrical schematic representation of the sensor is also shown in FIG. 1C. This is a representative implementation, which is not the only possibility, as will be discussed. This system includes the previously-discussed 180-degree out-of-phase excitation sources, 10 and 11, driving electrodes 12 and 14, which bracket sensing electrode, 13, and are equidistant from it, providing a net "dry"-condition zero-valued reference signal at electrode 13. The return for the sources, and the reference voltage for measuring the output at electrode, 13, is the system "ground". The shield electrode, 15, when included, and used with the circuitry shown here, is also connected to the system ground. Signal appearing at electrode, 13, in case of asymmetry of moisture in sensing regions, 32 and 33, which is represented by "raindrop", 19, is amplified, here, in single-ended inverting, transimpedance, "charge", amplifier, 20, synchronously-demodulated by multiplication in multiplier, 22, with the output of one of the excitation sources, here, 11, The output of the multiplier is low-pass-filtered in low-pass-filter block, 23, to remove the excitation-frequency carrier. The resulting low-pass-filtered, time-varying, "dc" level is then "full-wave-rectified" in an absolute-value amplifier circuit, 24, before being applied to voltage-comparator with moisture detection level input, 25. This detection electronics provides good immunity to non-signal, carrier frequency, interference, is relatively simple, and inexpensive, has been used with the moisture sensor of the invention, but other designs may also be used. Further, the electronics may change configuration, to suit changes in the electrode configuration, or connections to the electrodes, due to interchanging their functions. It is worthwhile to mention that a charge amplifier is a specific type of transimpedance amplifier, in which the feedback element is ideally a pure capacitance, so that with a pure capacitive source impedance, the voltage gain is given by the ratio of feedback to signal source internal capacitor, and inverted.

Figure 2A:
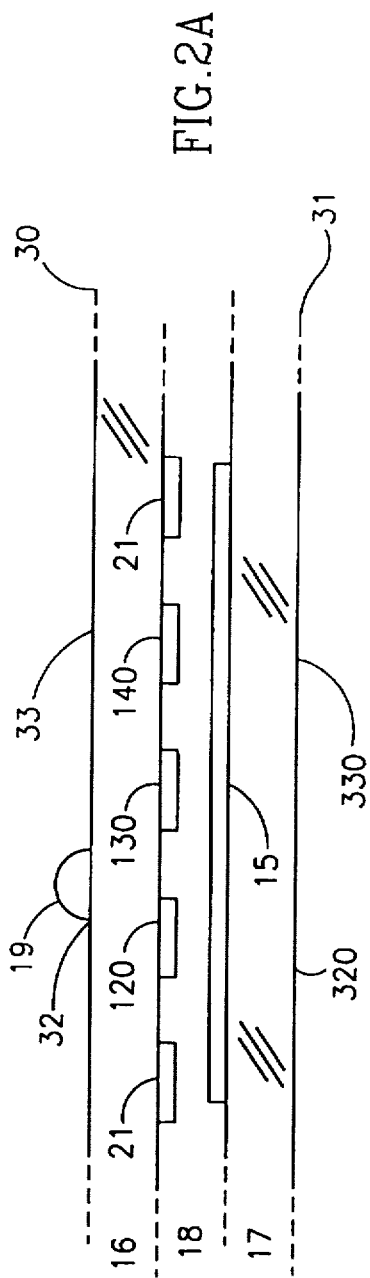
FIG. 2A is a modified, directional, differential, capacitive, moisture sensor.
Figure 2C:
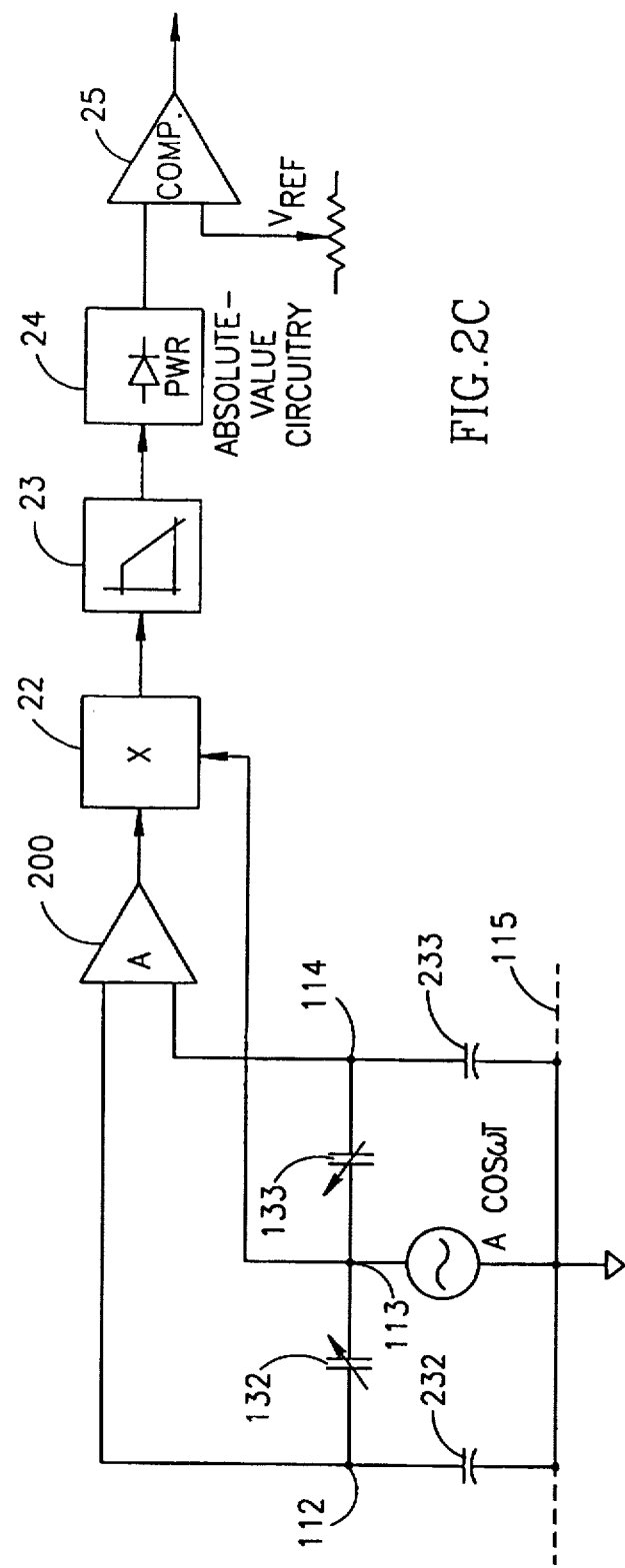
FIG. 2C is a schematic of the sensor of FIG. 2A, 2B.
Figure 2B:
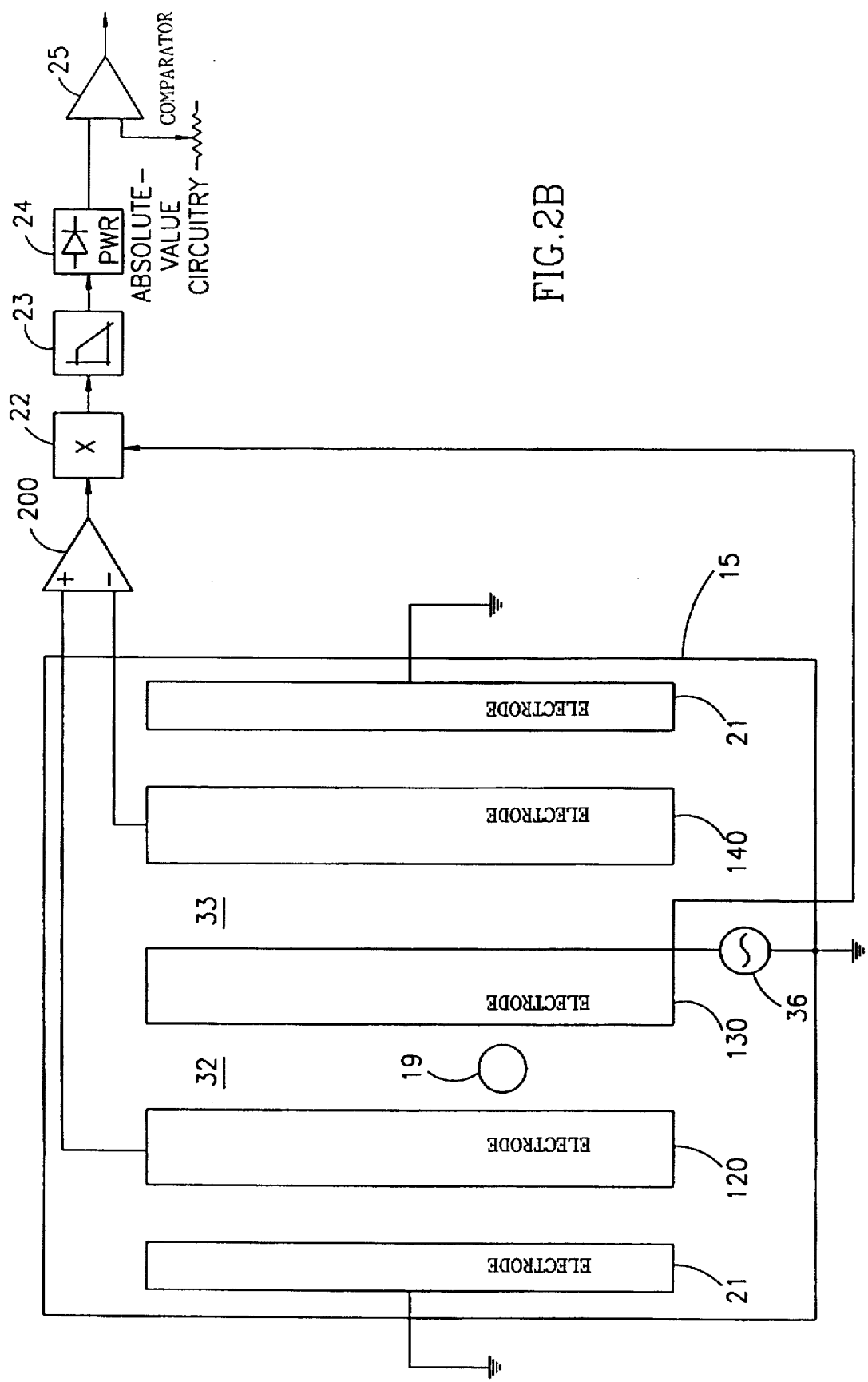
FIG. 2B is the modified, directional, differential, capacitive moisture sensor of FIG. 2A, with alternative configuration of excitation and sensing electronics.

Another possible configuration is shown in FIGS. 2A and 2B, and represented schematically in FIG. 2C. Elements of FIGS. 2A and 2B which have similar functionality to those of FIG. 1A and 1B, are numbered similarly. The function of electrode, 13, in FIG. 1A and 1B was as a single sensing electrode, with two excitation electrodes, 12 and 14. Here, 130 is a single excitation electrode, and electrodes 120 and 140, are a "true-differential" output-electrode pair. Here, the sensor must incorporate the shield, ground-plane, electrode, 15, which provides the directional properties of the sensor, since this serves as the return electrode for the excitation. This sensor now functions as a bridge, with four capacitance legs. The two sensing capacitances are between the active electrode pairs, 130 and 120, and 130 and 140, corresponding to sensing areas 32 and 33, respectively, as before. However, the capacitance from sense electrode, 120, to ground plane, 15, and the capacitance from sense electrode, 140, to ground plane, 15, provide the two reference capacitors for the bridge. These two capacitances depend on the plastic laminate as their dielectric. The single-ended-input, transimpedance, charge, amplifier, 20, of FIG. 1B has been replaced with the differential-input voltage amplifier, 200, of FIG. 2B. This may be realized as an instrumentation amplifier, as is well-known. The rest of the "receiver" electronics is the same. Also, two grounded "guard" electrodes, 21, have been added outside sense electrodes, 120 and 140, to shield them from the bottom of the substrate, in case the electrode, 15, does not extend far beyond the outer edges of sense electrodes 12 and 14. Alternatively, these guard electrodes may be bootstrapped with buffer amplifier to their adjacent sense electrodes. The single excitation source, 36, also provides the multiplier/demodulator reference input signal. The functionality of the sensor moisture sensor is the same as before, but the signal output is different, since the electrodes functionality is interchanged, necessitating a change in the sensor electronics. One possible advantage of this arrangement over that in FIGS. 1A and 1B, is that the differential-input amplifier, 200, may be less sensitive to radio-frequency interference (RFI) than the single-ended-input amplifier, 20. A further possible advantage of this arrangement over that of FIGS. 1A, 1B may occur in case of very large moisture signal. There may be some condition in which it is desired to add the signal at electrodes 120 and 140, in additional circuitry to provide an additional non-differential magnitude indication.

Figure 1D:
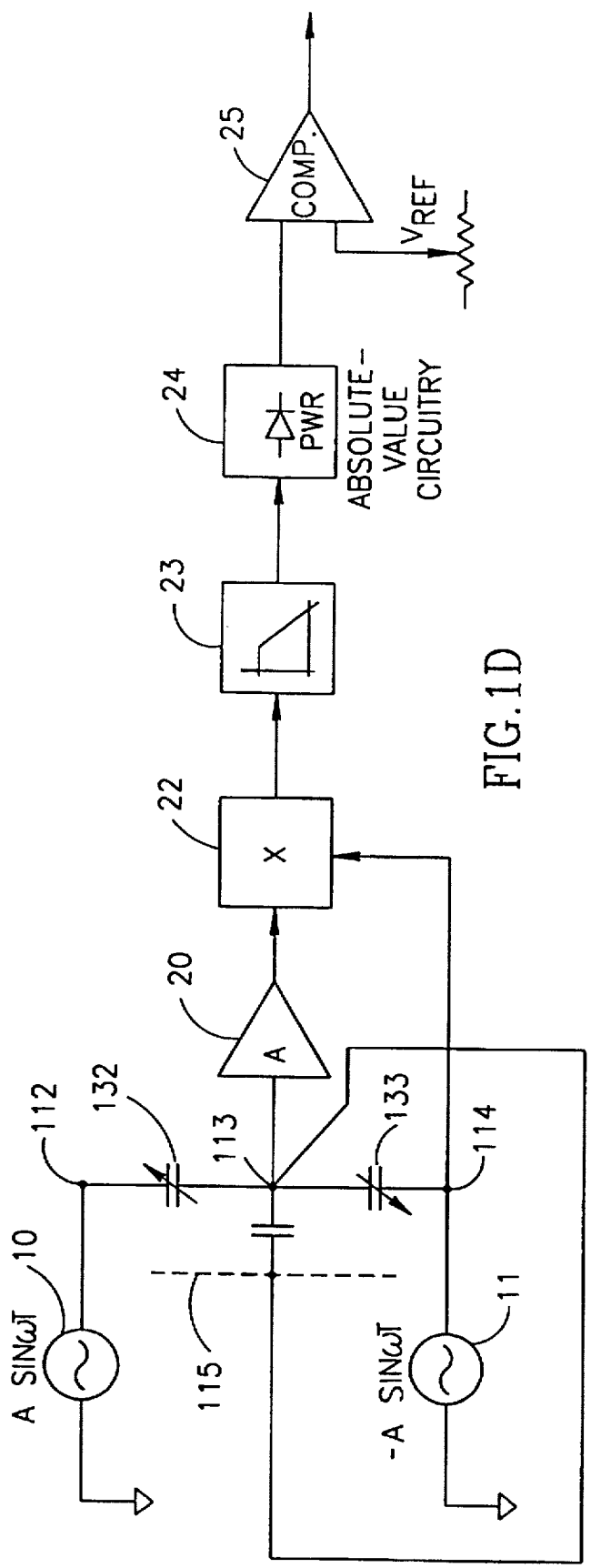
FIG. 1D is a schematic of the sensor of FIG. 1A, 1B.
Figure 1E:
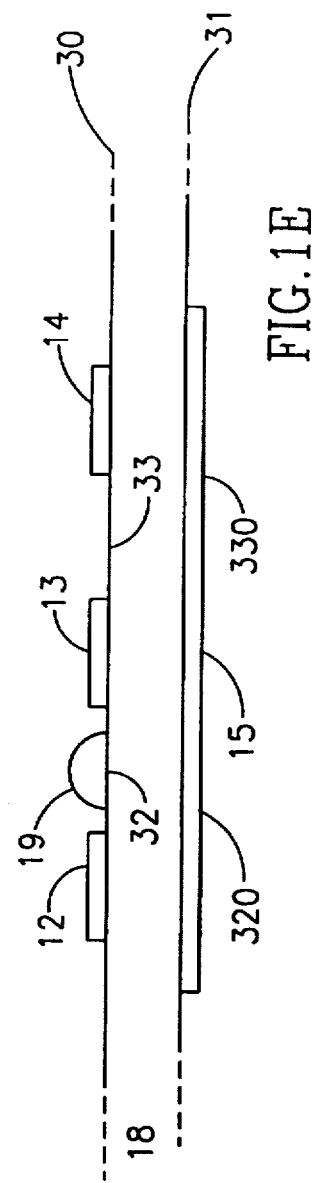
FIG. 1E is a standalone sensor.
Figure 3B:
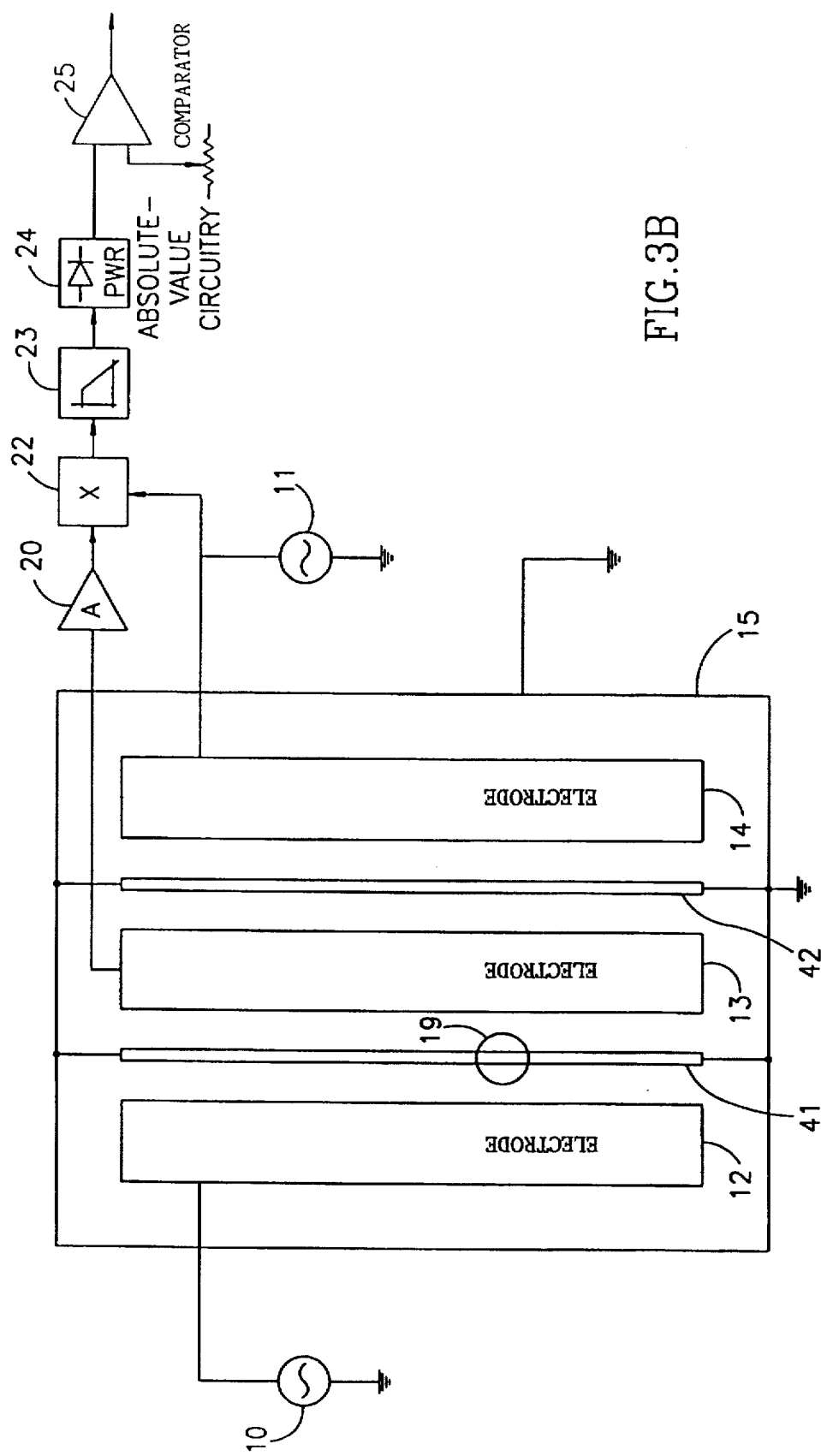
FIG. 3B is the sensor of FIG. 3A, with the electronics of FIG. 1A.

Yet another configuration is shown in FIGS. 3A and 3B. Here, a moisture sensor and electronics similar to that of FIGS. 1A and 1B, is modified by the addition of grounded shield electrodes, 41, and 42, between electrode pairs, 12 and 13, and 14 and 13, respectively, under sensing areas, 32 and 33, respectively. These shield electrodes reduce the coupling between the adjacent edges of the electrode pairs under the sensing areas, reducing the very-small non-moisture, "dry"-condition "offset" reference signal, hence, increasing the importance of the coupling via the sensing areas, 32 and 33, in providing a signal to sense electrode, 13. In practice, electrodes 41 and 42 should probably be a guard ring, surrounding electrode 13, and not two separate conductive strips. This guard ring may be "bootstrapped", i.e., driven from a voltage-follower output, whose input is connected to electrode, 13. This should be a more-effective capacitance-reduction technique than just grounding the guard ring. The shield electrode, 15, in FIGS. 3A and 3B, and in FIGS. 1A and 1B may also be bootstrapped. This bootstrapping would be useful if the transimpedance "charge" amplifier, 20, is replaced by a voltage amplifier, since then there would otherwise be capacitive division of the signal at sense electrode 13, concerning bootstrapping of electrode 15 in FIGS. 1A and 3A, refer to FIG. 1C. The electrical schematic shows nodes 112, 113, and 114 representing points of connection to active electrodes 12, 13, and 14 respectively, and 115, corresponding to connection to plate 15. There will be a parasitic capacitance from plate 13 and node 113, to plate 15 and node 115. This capacitance forms a voltage divider to plate 15 and node 115, which attenuates the input signal to amplifier 20, present on plate 13, node 113, if plate 15, node 115, is grounded. But if plate 15, node 115, is bootstrapped to plate 13, node 113, with a buffer amplifier (1115, FIG. 1D), then the voltage on nodes 113 and 115 is equal, and there is no capacitive divider action, so a larger signal, the maximum signal possible at node 113, will be provided to amplifier 20 by electrode 13.

Figure 6A:
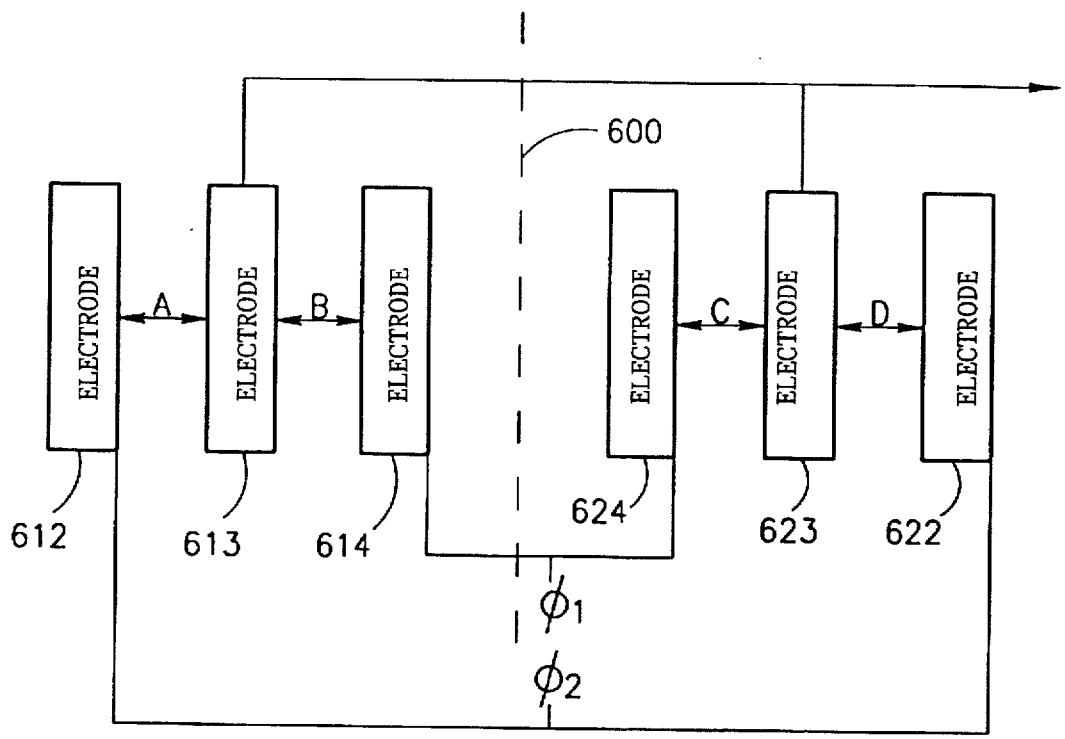
FIG. 6A is an interconnection of a pair of unit sensors of FIG. 1A in a beneficial manner.
Figure 6B:
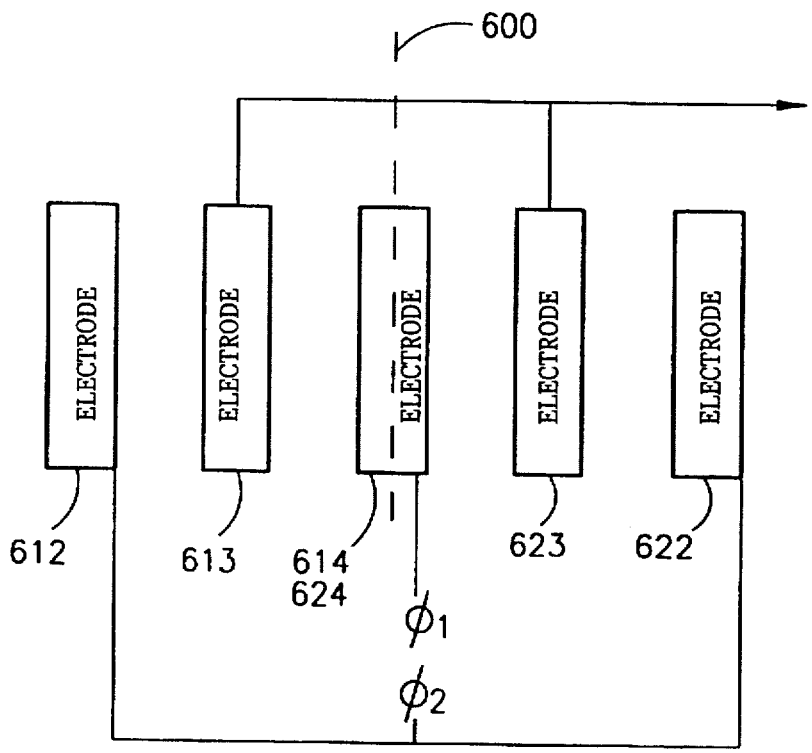
FIG. 6B is a simplification of FIG. 6A.

Yet another configuration is shown in FIG. 6A, and simplified in FIG. 6B. This composite sensor is the combination of two unit sensors of the type of FIG. 1A. In the unit sensor of FIG. 1A, if a stress applied to the substrate results in an expansion, for example, of the distances between electrode pairs 12 and 13, and 13 and 14, then the moisture-sensing sensitivities in regions 32 and 33, respectively, will change. If there is a uniform expansion, i.e., an equal increase in the two electrode-pair separations, then the sensor remains balanced, and no false output results. If, however, there is a gradient, a non-uniform expansion, so that the separation between one pair of plates is greater than that between the other pair, then a false output signal will result. The configuration of FIGS. 6A, 6B, solves this problem, by interconnecting two unit sensors, in such a way that the expansion gradient will be cancelled. With respect to FIG. 6A, electrodes 612 and 622 correspond to electrode 12 in FIG. 1A; electrodes 613 and 623 correspond to electrode 13 in FIG. 1A; electrodes 614 and 624 correspond to electrode 14 in FIG. 1A. Therefore the signal output due to moisture in the sensing regions between electrodes 612 and 613, and 622 and 623, add together, and the signal output due to moisture in the sensing regions between electrodes 613 and 614, and 623 and 624, add together. The difference between these added moisture-signal pairs provides the moisture-present indication as explained above. Now, if there would be a uniform expansion of the sensor, increasing all four spacings, labeled, a, b, c, d, the sensor remains balanced; and also, unique to this parallel interconnection of two unit sensors, in case of a gradient expansion increase of spacings, the sensor also remains balanced. This is easily seen as follows: assume a gradient expansion such that the distance increase at a is greater than at b, which is greater than at c, which is greater than at d. But the gradient is assumed to be uniform, so the distances (a+d)=(b+c), and the net combination sensor remains balanced when subjected to gradient stress. To achieve this, the two unit sensors must be symmetrically placed about a common center line, 600. Since electrodes 614 and 624 in FIG. 6A are adjacent, and bracket the outer line, 600, and are connected together, the two sensors of FIG. 6A may be made more compact by combining the two electrodes, 614, and 624, into one electrode as in FIG. 6B, in which the center line, 600, now bisects the one combined electrode. This illustrates one composite sensor with greater immunity to substrate lateral dimensional variations than one unit sensor alone. Similar argument also applies to a gradient thickness change.

Figure 7A:
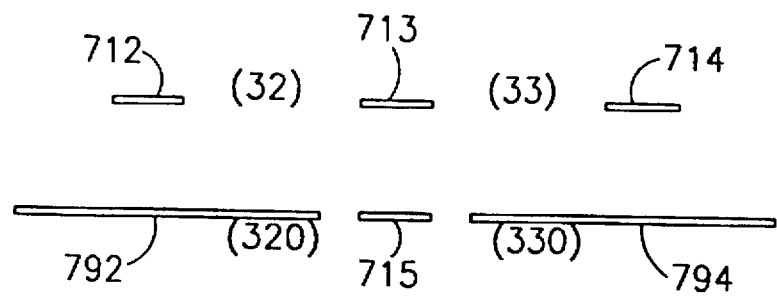
FIG. 7A is a modified sensor based on that of FIG. 2A.
Figure 7B:
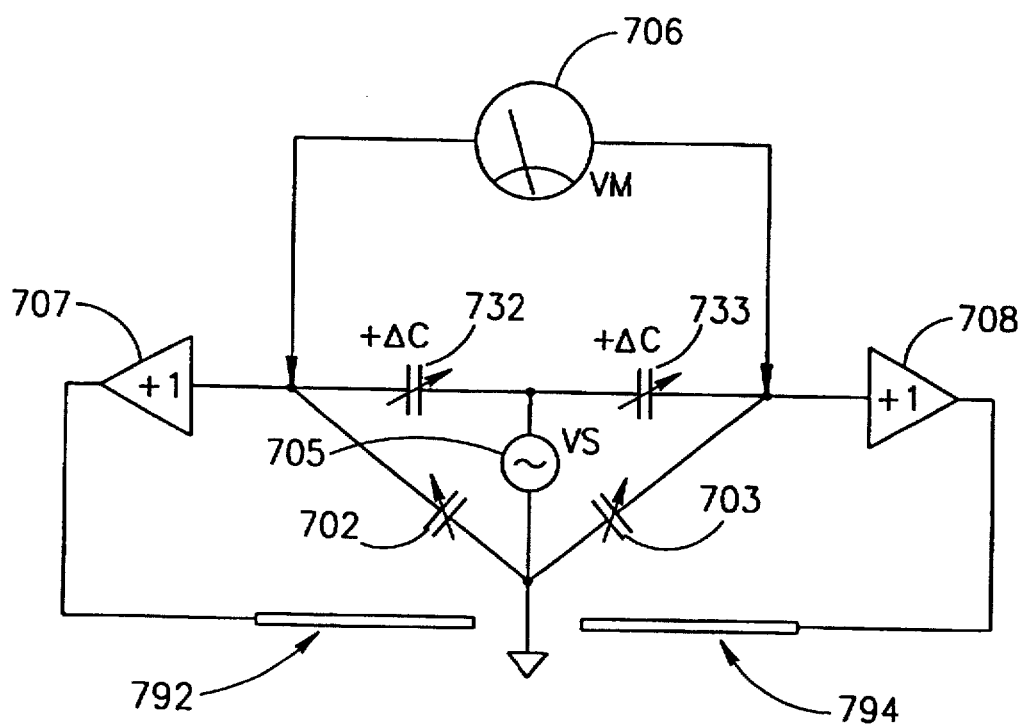
FIG. 7B is a circuit representation of the sensor of FIG. 7A.

Yet another configuration is shown in FIG. 7A, and an electrical circuit representation of it, in FIG. 7B. This is a modification of the sensor of FIG. 2A, in such a manner that the same gradient-dimensional-change problem solved above in FIG. 6A, 6B by a combination of two sensors, is solved in one sensor. In FIG. 7A, electrodes 712, 713, 714, and 715, correspond to electrodes 120, 130, 140, and 15 in FIG. 2A. In FIGS. 2A, 2B, electrode 15 is both the shield against sensing of moisture in regions 320 and 330, and also the electrical ground return for excitation source 36. The electrical equivalent circuit in FIG. 2C shows that two capacitors, 132, and 133 vary with moisture in regions 32 and 33, respectively. Capacitors, 232 and 233, from electrodes 120 to 15, and 140 to 15, respectively, serve as reference capacitors for the capacitor bridge circuit, and do not change value with moisture. This sensor has the same dimensional-change properties as the sensor of FIG. 1A.

Now in the sensor of FIG. 7A, electrode 715 has been reduced in the width to correspond approximately to the width of electrode 713. Electrode 715, therefore, will be affective as the electrical return node for the bridge, and the capacitances, 702 and 703, in FIG. 7B will be reduced compared with capacitances, 232 and 233, in FIG. 2C. But, capacitance 702 will vary with dimensional changes in the same manner as capacitor 732, and capacitor 703 will vary with dimensional changes in the same manner as capacitor 733, so the reference capacitance corresponding to each sensor capacitance varies with stress proportionally, and the bridge remains balanced for gradient dimensional changes, as well as for uniform dimensional changes. Thus the sensor of FIG. 7A is an improvement in this respect.

The problem of providing directionality is solved by adding shield electrodes, 792, and 794, below sensing electrodes, 712, and 714, respectively, and bootstrapping them with unity-gain amplifiers, 707, and 708, respectively, to restore effective shielding against moisture in regions 320 and 330. The shield electrode, 15, of FIGS. 2A, 2B, has thus been replaced by a multiple-section shield, or multiple shields, segments, portions of which, are either grounded or bootstrapped to their corresponding sensing electrodes, as appropriate to the sensor design.

Yet another configuration results from just modifying dimensions of the sensor active electrodes to take into account the physical limitations of the specific manufacturing process used, for example, in the case of lamination in an automobile windshield, as has been discussed. Ideally, a combination of a perfect windshield and a uniform layer of moisture would result in zero output signal. When used as a windshield fog sensor, a situation may occur, that the fog is sufficiently uniform as to create a very small signal. In other words, for the sensor to respond to a uniform moisture layer, the sensor should not be perfectly balanced. This required imbalance may be implemented either mechanically or electronically. In practice, the windshield laminates thicknesses are not perfectly uniform. Therefore, the distance between the moisture layer and the electrode plane is not fixed, and the capacitively induced currents do not cancel, even with a uniform layer of moisture. Thus, in a realistic sensor, a signal will be generated even when the moisture layer is perfectly uniform. On the other hand, such a sensor also responds to common mode effects such as heating of the windshield, but in practice, it has been found that there is no contradiction; and the amount of nonuniformity in practical windshields is sufficiently small to eliminate false signals due to temperature and mechanical stresses, yet sufficiently large to sense even a uniform layer of fog.

In a preferred embodiment of the invention, the sensor is deliberately made slightly asymmetrical, for example, by making the lengths of the opposing excitation electrode slightly different, to ensure that even when the laminates happen to be uniform in thickness, a uniform moisture layer could be sensed. This method applies to any of the sensors of the present invention, as it is inherent in the structure.

Figure 8:
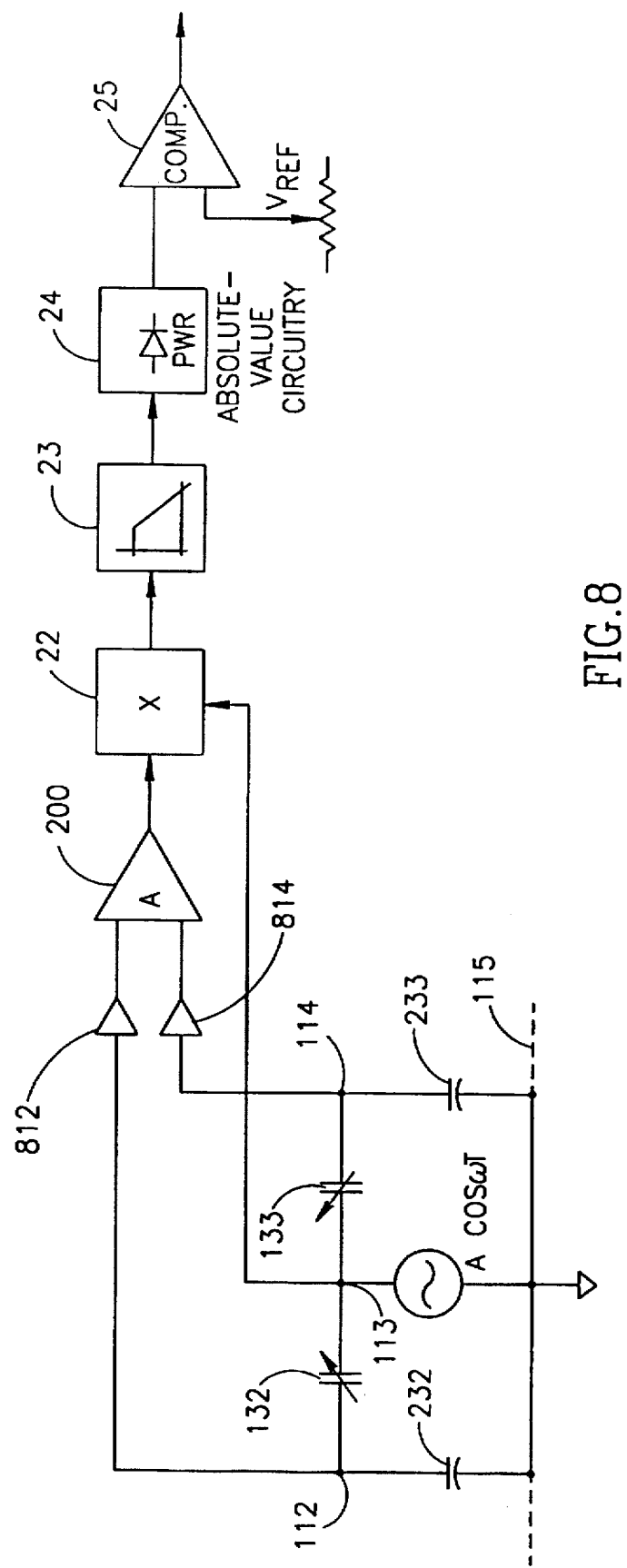
FIG. 8 is as FIG. 2C but with the inclusion of a pair of amplifiers.

Asymmetry of output in the case of a mechanically perfectly-balanced sensor may also be provided electronically, as mentioned above. This method applies in the case of sensors of the types shown in FIGS. 2A, 2B, and FIGS. 7A, and shown schematically in FIGS. 2C, and 7B, respectively. These sensors are "bridge" sensors, in which the output is taken differentially between two output nodes. The electronic imbalance is provided simply by providing different electronic gains to the signals available at the two bridge output nodes, for example with separate pre-amplifiers 812 and 814 (FIG. 8), and applying the outputs of these pre-amplifiers to the differential amplifier that would otherwise have been directly connected to the two bridge output nodes.

Figure 9A:
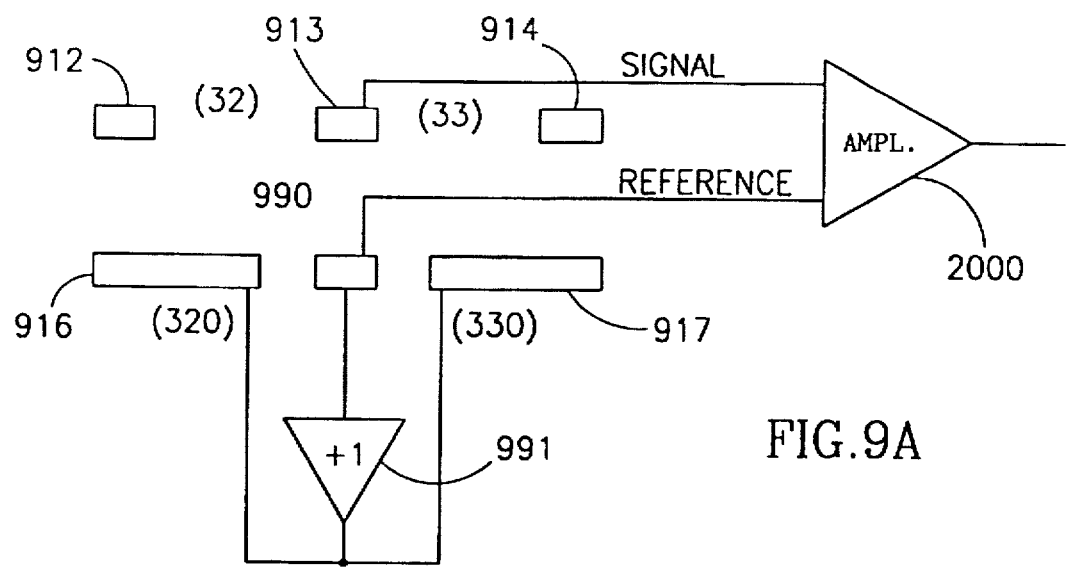
FIG. 9A is a modified sensor based on that of FIG. 1A.
Figure 9B:
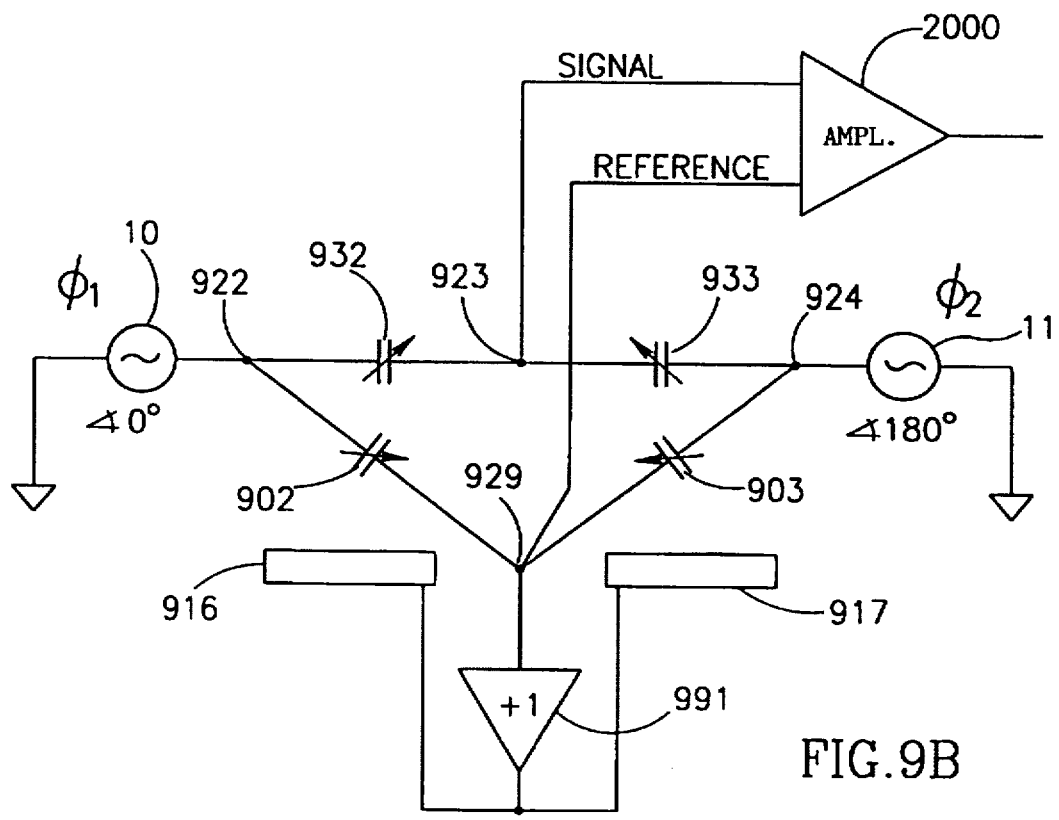
FIG. 9B is an electrical representation of the sensor of FIG. 9A.

Yet another configuration is shown in FIGS. 9A and 9B. Here, electrodes 912 and 914 are driven by balanced, 180-degree out-of-phase sources 10 and 11, and the signal output is taken at electrode 913, as in the FIG. 1A, etc., sensor. This version of the sensor includes an active electrode, 990, below electrode 913. Electrode 990 receives a "dry" reference signal depending on a capacitive-divider effect between capacitors 902 and 903, whose values will also be dimensionally-dependent, substantially similarly to capacitors 932 and 933, which are the capacitive couplings via the moisture-sensing regions 32 and 33, respectively. An amplifier, 2000, with inputs connected to electrodes 913 and 990, nodes 923 and 929, respectively, will develop a moisture-dependant output signal; but, since both lateral capacitive dividers will have similar substrate-dimensional variation "dry" capacitance sensitivities, the sensor output will be substantially independent of substrate-dimensional variation. The addition of shield electrodes 916 and 917, below electrodes 916 and 917, respectively, and bootstrap amplifier, 991, bootstrapping electrodes 916 and 917 to active reference electrode 990, node 929, provides sensor directionality. Without electrodes 916 and 917, and bootstrap amplifier 991, as above, the sensor could be used to differentially sense moisture on an upper moisture-sensitive surface versus moisture on a lower moisture-sensitive surface, but this is not the goal in the automotive windshield application.

The relative dimensions of the electrodes 916, 917, and 990, may be adjusted to minimize the actual substrate dimensional sensitivity. If a charge amplifier is used, then the reference output will be its reference, rather than system signal ground. Alternatively, a differential voltage amplifier may be used.

An improved differential capacitive moisture sensor has two preferably-equal capacitances due to the physical design of the capacitor plates, as will be described with respect to FIG. 10C. Since the capacitances are equal, the two capacitances have equal "dry" sensitivities when excited by 180-degree out-of-phase sources, as in FIG. 10B—both will couple equal amounts of charge into the summing junction of charge amplifier, 20, but with opposite phase, so the net sensor dry output will be zero. Since the two capacitances are equal-value, using the same dielectric, temperature variations in dielectric constant of the glass will be cancelled, since the capacitances will vary together with temperature. But the "wet" moisture sensitivities are different, due to the capacitor design, as will be described with reference to FIG. 10C.

As is well known, the capacitance of a parallel-plate capacitor is ideally proportional to A/d, where is the area of the capacitor plate, and d is the distance between the two plates of the capacitor. If two capacitors have equal A/d, and share the same dielectric, the two capacitances will be equal. But the plate areas, A, and plate separations, d, may be designed to be different, to meet some desired design goal. This is the case here.

Figure 10A:
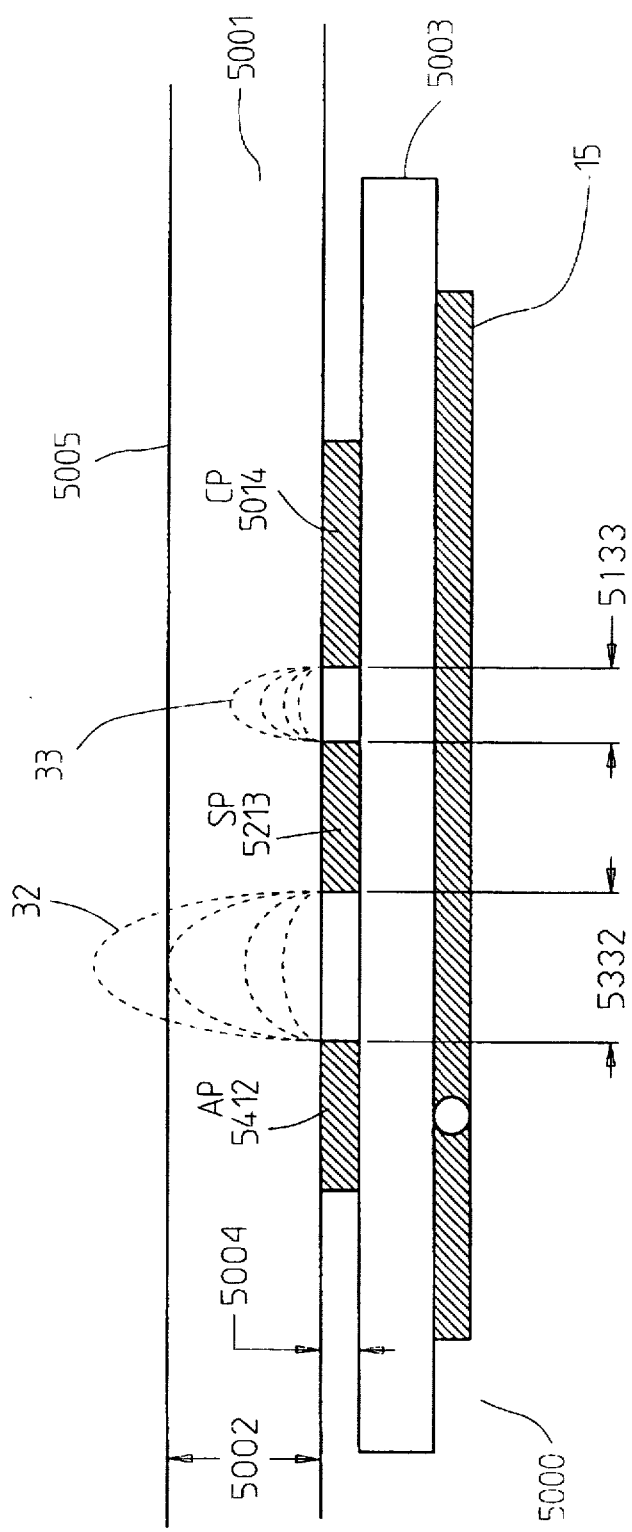
FIG. 10A is a differential moisture sensor with equal dry capacitances, and with unequal moisture sensitivities.
Figure 10B:
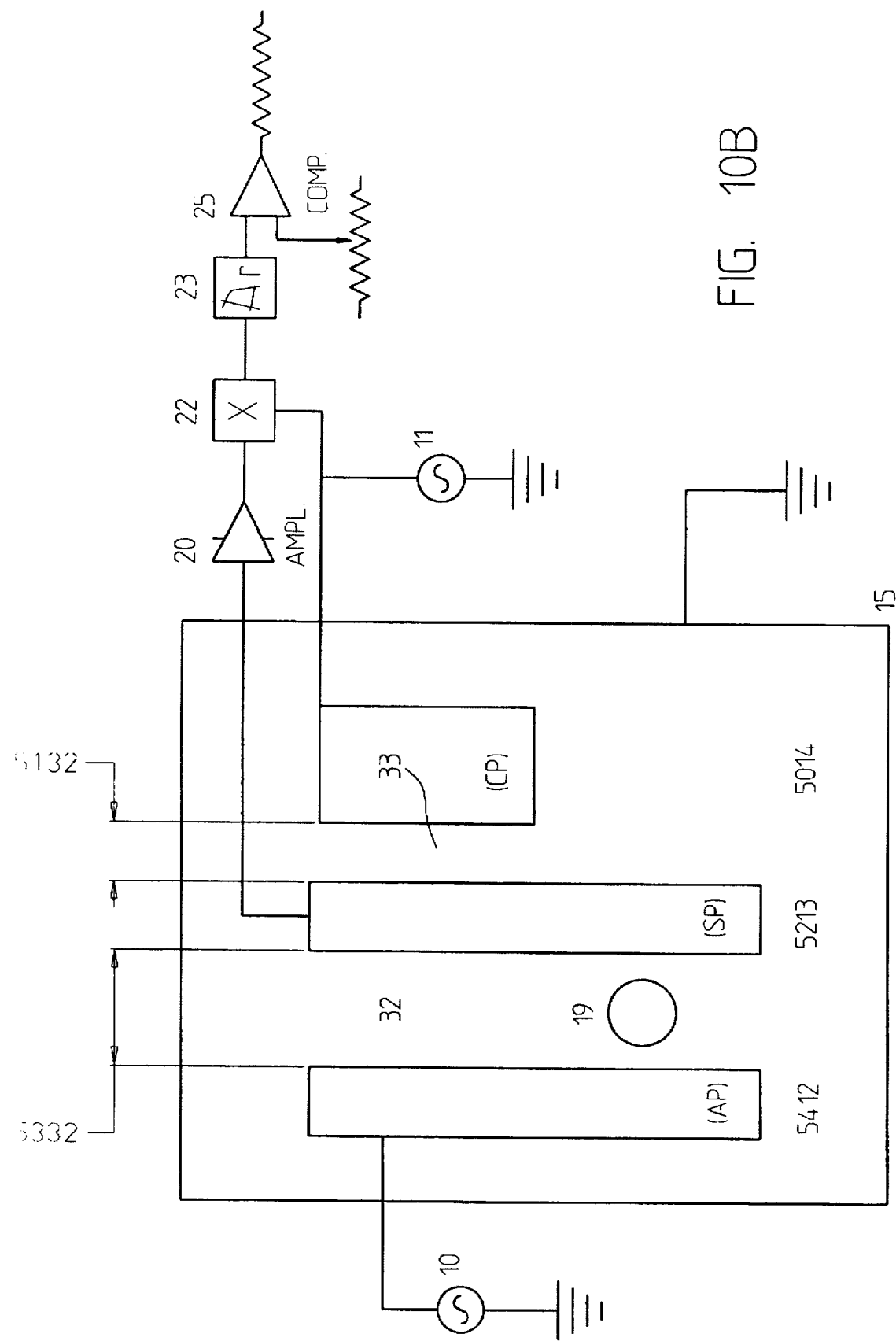
FIG. 10B is the sensor of FIG. 10A, with one possible configuration of excitation and sensing electronics.
Figure 10C:
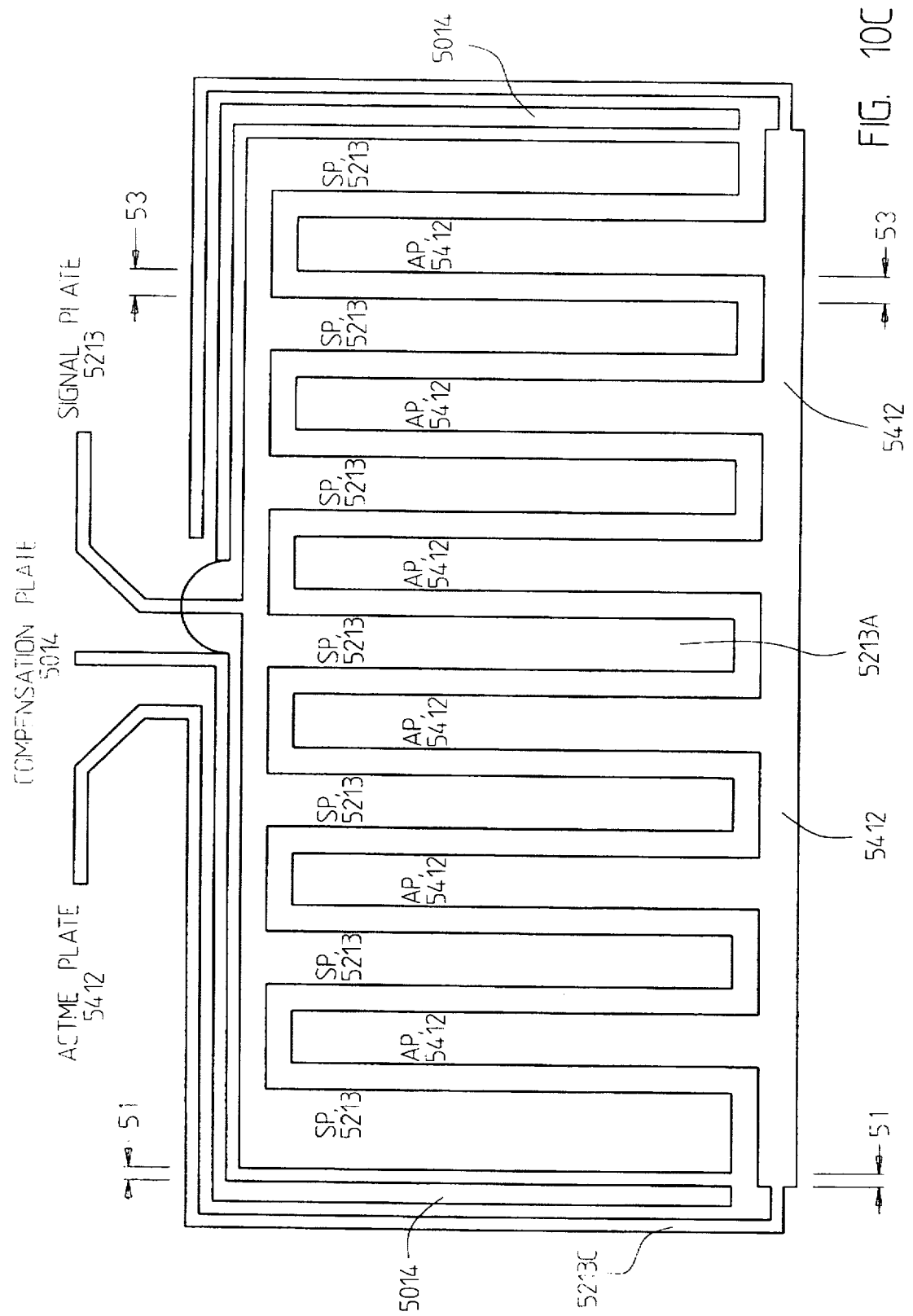
FIG. 10C is a pattern for a sensor as in FIG. 10A.

Referring now to FIG. 10C, a printed circuit pattern is shown, with three "land" areas, which may be used to fabricate three capacitor plates. Signal Plate, 5213, is shared between two capacitors. The Signal Plate, 5213, (SP) has two edges, a first edge adjacent to the pattern of Active Plate, 5412, (AP) and a second edge adjacent to Compensation Plate, 5014 (CP). Thus the pattern of FIG. 10C represents two capacitors, with a shared plate, SP, 5014.

It will be appreciated, that when a pattern such as in FIG. 10C is printed, the material has a finite thickness. The area of each capacitor plate in FIG. 10C is not the area that we see looking at the printed pattern. Rather the area of each capacitor plate may be calculated as approximately equal to the product of the material thickness times the length of the pattern edge which is adjacent to the other plate with which it is to make up a capacitor. Thus Signal Plate, 5213, has two edges, 5213A, and 5213C, adjacent to Active Plate, 5412, and Compensation Plate, 5014, respectively. When the pattern is fabricated, the material thickness is ideally uniform, so the all the plate edges have the same height up from the paper in the FIG. 10C. The length of SP edge, 5213A, opposite AP, 5412, is layed out to be much longer than the length of SP edge, 5213C, opposite CP, 5014. Thus the plate area of the capacitor between SP, 5213, and AP, 5412, is much greater than the plate area of the capacitor between SP, 5213, and CP, 5014. The separation, 5332, between SP, 5213, and AP, 5412, is much greater than the separation, 5133, between SP, 5213, and CP, 5014. The dimensions a re designed, in fact so that the capacitances of the two capacitors are substantially equal. Thus when AP, 5412, and CP, 5014, are excited by equal-amplitude, 180-degree out-of-phase excitation, the difference between the signals coupled from the two excitations through their respective capacitors will be substantially zero.

FIG. 10A shows a cross-section of the sensor of FIG. 10C. Sensor, 5000, includes SP, 5213, AP, 5412, and CP, 5014, as in FIG. 10C. The three electrodes are printed on the first surface of a substrate, 5003, typically mylar, and a shield electrode, 15, has been added on the second "reverse" surface of substrate, 5003. SP, 5213, and AP, 5412, are separated by distance, 5332, and SP, 5213, and CP, 5014, are separated by distance, 5133. The printed pattern has a material thickness, 5004. The mylar substrate is in contact with a first surface of glass, 5001, which has a thickness, 5002. Glass, 5001, serves as the dielectric of the two glass-dielectric sensor capacitors. Since the two capacitors have been arranged by design, by the geometry of the pattern of FIG. 10C to have the same ratio of A/d, even with different respective values of A and d, and since the same glass with the same thickness, and with the same dielectric constant is used for both capacitors, the two capacitors have substantially the same capacitance. Now, to complete the sensor design, the choice of plate separations, 5332, and 5133, is related to the thickness, 5002, of glass dielectric, 5001, as follows. The separation, 5133, between the two capacitor plates, SP, 5213, and CP, 5014, is shown to be small compared to the thickness of glass, 5001. As a result of this choice, the fringing field between the two plates will be substantially contained inside glass dielectric, 5001. This means the capacitance between SP, 5213, and CP, 5014, will not be affected by moisture on second surface, 5005, of glass dielectric, 5001, so the dry and wet capacitances will be substantially equal. On the other hand, the separation, 5332, between the two capacitor plates, SP, 5213, and AP, 5412, is shown to be comparable to the thickness of glass, 5001. As a result of this design choice, the fringing field between the two plates, SP, 5213, and AP, 5412, will extend somewhat out through the second surface, 5005, of glass dielectric, 5001, and the value of capacitance between SP, 5213, and AP, 5412, will be affected by the presence of moisture on the second surface, 5005, of glass dielectric, 5001. Thus, the two capacitors of the differential capacitance sensor of FIGS. 10A–C will have equal "dry" capacitances, but different "wet" capacitances. The moisture-insensitive capacitor is the capacitance between SP, 5213, and CP, 5014. The moisture-sensitive capacitor is the capacitance between SP, 5213, and AP, 5412. Thus, the active moisture sensing area will be the area, 5332, between SP, 5213, and AP, 5412, on the second surface, 5005, of dielectric glass plate, 5001. For example, a differential moisture sensor as disclosed may be realized by the use of a 3-mm thick glass window laminate, with electrodes having dimension 5133 equal to 1 mm, and dimension 5332 equal 3 mm. Any desired combination of sensitivities of the differential capacitive moisture sensor to moisture in regions 32 and 33 may be designed by designing the ratio of electrode separations, d, to dielectric thickness.

FIG. 10B, gives a representation of the sensor of FIG. 10C, with associated electronics. FIG. 10B is similar to FIG. 1B, and the sensor and electronics have similar functionality, with a few exceptions, to be discussed. First, it is important to note the presence of grounded shield plate, 15, in FIG. 10C, with the same function as in FIG. 1B, to provide sensitivity of the sensor in one direction only. Thus when moisture sensor, 5000, is assembled inside an automotive windshield sandwich glass, for example, the sensor, 5000, will only be sensitive to moisture on the second surface of the glass against which the electrodes, 5213, 5014, and 5412, are located. A difference between the circuits of FIGS. 1B and 10B, is the absence of full-wave-rectifier, absolute-value circuit, 24, in FIG. 10B. Since in the sensor of FIGS. 10A–C, only one of the two capacitances is moisture-sensitive, the output of synchronous-demodulator, multiplier, 22, will be unipolar, not requiring an absolute-value circuit to provide a unipolar signal to comparator, 25. The sensor illustration of FIG. 10B shows the reduced gap width, 5133, and edge length of capacitor plate, CP, 5014, which maintain the same A/d ratio as for CP, 5014, as for AP, 5412, while providing substantially zero moisture sensitivity in region 33, with respect to the moisture sensitivity in region 32.

Preferably, amplifier, 20, represents a charge amplifier, and the input connection to amplifier, 20, in FIG. 10B represents the virtual earth, summing junction, of charge amplifier, 20. Briefly, sources 10 and 11 are excited 180-degrees out-of-phase, so that with equal "dry" sensor capacitances, the net charge coupled into the virtual earth, summing junction, of charge amplifier, 20, is zero in the case of no moisture in regions 32 and 33. When moisture, represented by "rain-drop", 19, is present in region 32, or in both regions 32 and 33, there will be a difference signal coupled into the input of amplifier 20, since the moisture in region 32 will result in greater dielectric constant than that previously in the fringing field region between SP, 5213, and AP, 5412, which extends through glass dielectric, 5001, into region 32. Thus the capacitance between SP, 5213, and AP, 5412, will be increased, providing increased signal coupling from source 10 to the input of amplifier, 20.

The various multiple-sensor layout options described earlier in FIGS. 6A–B may also be applied to the sensor of FIGS. 10A–C. Similarly, variations in the electronics may also be employed with the sensor of FIGS. 10A–C.

The preferred method of assembly is to fabricate, for example, by plating, the electrode pattern on a thin mylar sheet, as illustrated in FIG. 10C, using a transparent material. The thin mylar sheet is placed between the layers of the sandwich glass, and molded into the sandwich glass at the time of manufacture. The mylar preferably has an extended portion, "extension", which contains a printed wiring pattern, thus providing a built-in "ribbon cable", which extends out of the edge of the sandwich glass, for making the required electrical connections to sensor 5000. The curved "wire" pattern in FIG. 10C, which crosses over the signal plate connection, and which connects the two compensation plate areas, represents an additional "jumper" connection, not located in the plane of the printed pattern, which is necessary for the use of the electrode layout shown.

Notice that signal plate, SP, 5213, serves as two capacitor plates, since SP, 5213, is shared between the two capacitances formed over sensing regions 32 and 33.

It will be appreciated that since both capacitances of differential capacitive moisture sensor, 5000, share the same dielectric, 5001, that the sensor, 5000, is insensitive to the variations of dielectric constant of dielectric, 5001, over temperature, while providing a sensor with very high moisture sensitivity, since the sensor output signal is purely a moisture signal.

A further improvement to the differential moisture sensor of the present invention will now be described with reference to FIGS. 11A–11C.

There are situations where it is desirable to determine whether the moisture sensed is liquid water or solid ice or snow, or a mixture of ice and snow, commonly called "slush". For example, it may be desirable to clear snow collected by the wiper on the lower portion of the windshield. In this case an "ice sensor", which detects "solid-phase water" is useful to detect the presence of snow, in order to automatically melt the snow by operating an electric grid heater.

It was found that there is a way to distinguish between solid-phase and liquid-phase water. This based on the different dielectric constants of water in the two different phases, and more importantly, on the frequency dependence of the dielectric constant of ice and snow. FIG. 11A shows the dependence of the dielectric constant of ice as a function of temperature and frequency. It is seen that for any temperature, the higher the frequency, the lower the dielectric constant. On the other hand, the dielectric constant of liquid-phase water is slightly dependent on temperature, but is independent of frequency up to the high MegaHertz range. As a result, it is possible to capacitively sense the presence of solid water by varying the excitation frequency and observing the output signal. If there is only liquid-phase water in the vicinity of the sensor the output signal will not change with the frequency. On the other hand, if there is solid-phase water in the vicinity of the sensor the output signal will vary with the frequency. The graph of FIG. 11A was taken from *International Critical Tables of Numerical Data, Physics and Technology*, Vol. 6, Mc-Graw-Hill Book Co., first edition, '29, page 78. In the same reference a formula describing the dependence of the dielectric constant of liquid-phase water appears on the same page. For liquid-phase water, dielectric constant=80−0.4(T−20), where T is in degrees Celsius. Thus the dielectric constant of water=80, T=20° C., and the dielectric constant of water=88, T=0° C. This is valid independent of frequency from DC to hundred Megahertz.

As previously stated, liquid-phase water has a dielectric constant of about 80. Curve 2, the −2 degrees Celsius curve, of FIG. 11A shows that for ice at a temperature of −2 degrees Celsius, at low frequencies, the decrease of dielectric constant due to the phase change from liquid to solid water is small, with the dielectric constant falling about 25% to a value of about 60 at about 2 kHz. Also, the minimum dielectric constant for solid-phase water at a temperature of −2 degrees Celsius is reached at frequencies greater than about 40 KHz, and is about 5.

Figure 11A:
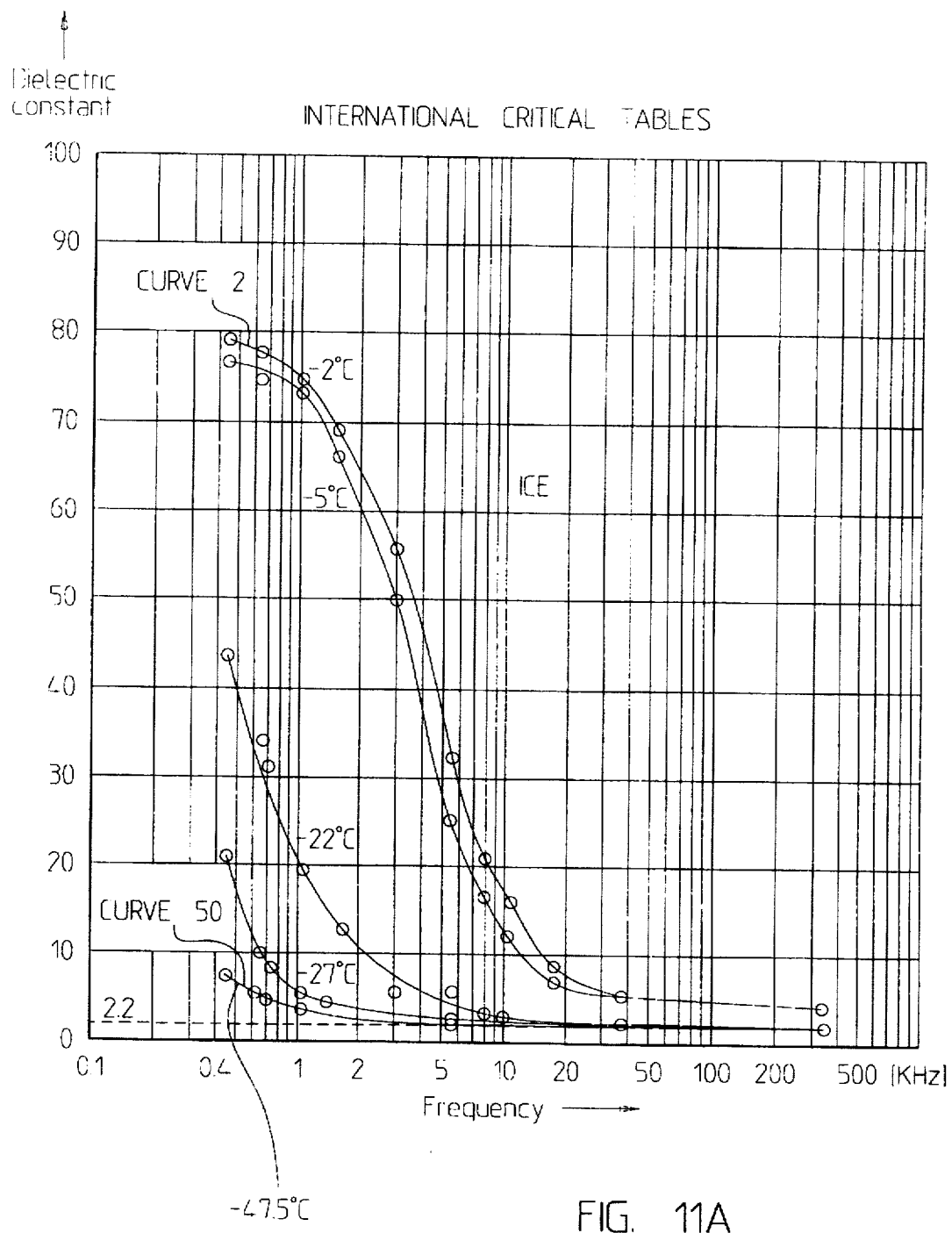
FIG. 11A is a handbook plot of dielectric constant of ice versus frequency, with temperature as a parameter.

Curve 50 of FIG. 11A, the −47.5 degrees Celsius curve, shows a dielectric constant of about 8 at 450 Hz, falling to a minimum of about 2.2, for frequencies above about 40 kHz. It appears that Curve 50 should extrapolate to a dielectric constant in excess of probably 15 at a frequency of about 200 Hz. 50 kHz is a convenient upper-frequency choice.

For reliable ice detection at all temperatures from about −50 degrees Celsius to about −2 degrees Celsius, it is necessary to select two dielectric constant measurement, that will show a decrease of dielectric constant when increasing the measurement frequency from the lower measurement frequency to the higher measurement frequency. A choice of lower measurement frequency of 200 Hz, with a choice of upper measurement frequency of greater than, say 40 kHz, should result in a ratio of low-frequency signal to high frequency signal of at least three, corresponding to the ratios of dielectric constants. Since the minimum dielectric constant is known to be about five at −2 degrees Celsius, the resulting output signal may be reliably predicted, and a fixed-threshold comparator may be used in the electronics, to detect presence of ice. If the minimum signal level would not be well-known, the ratio of the two signals could still be taken in the electronics following the sensor, and an ice/no-ice decision could be made based on the ratio of the signals.

Figure 11B:
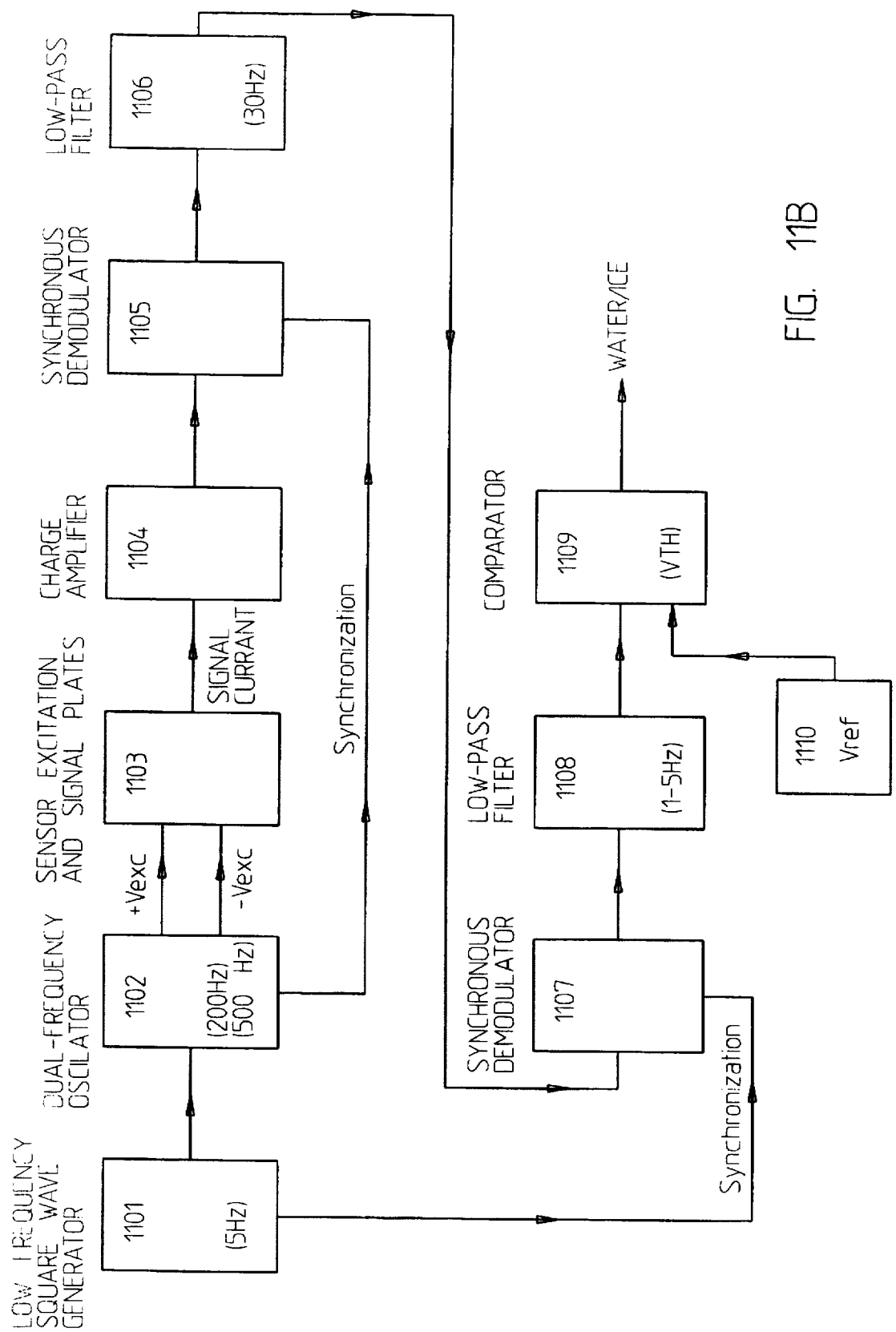
FIG. 11B is a block diagram of the ice sensor system.

FIG. 11B shows a block diagram of the implementation of the ice-detection method of the present invention. Low-frequency square-wave generator "control clock", 1101, provides an output which causes dual-frequency oscillator, 1102, to alternate between the two output frequencies of dual-frequency oscillator, 1102. As discussed above, the two frequencies are preferably about 200 Hz and about 50 kHz, with a "control clock" square-wave oscillator frequency of about 5 Hz. Dual-frequency oscillator, 1102, is shown to preferably provide push-pull, 180-degree out-of-phase outputs to preferably drive a differential window moisture detector, 1103, as in the present invention. However, the "ice detector", solid-phase/liquid-phase detector of the present invention may alternatively employ a "single-ended", non-differential sensor, such as the single-ended sensing plates of the rear window automatic defrost described in sister application, *A Window Capacitive Moisture Sensor*, U.S. Pat. application Ser. No. 08/625,473, to Yishay Netzer. Whichever moisture sensor is used, the moisture sensor, 1103, output signal current is fed to charge amplifier, 1104, summing junction input. Charge amplifier, 1104, typically provides a voltage output to synchronous demodulator, 1105. The output of capacitive moisture sensor, 1103, is demodulated in synchronous demodulator, 1105, and low-pass filtered in low-pass filter, 1106. The upper cut-off frequency of low-pass filter, 1106, is preferably chosen to be the square root of the product of the clock frequency of 1101, and the lower output frequency of dual frequency oscillator, 1102. For the numbers given, therefore, low-pass filter, 1106, preferably has an upper cutoff frequency of about 30 Hz. The output of low-pass filter, 1106 is a square wave alternating between two output voltage levels. The higher output voltage level is due to the sensor output signal at the lower measurement frequency, and the lower output voltage level is due to the sensor output signal at the higher measurement frequency. This is the case, since, as we saw in the discussion of FIG. 11A, the capacitive sensor output signal will be proportional to dielectric constant of the ice, and dielectric constant of the ice falls as frequency increases, as shown in FIG. 11A. Now to make the detection of the presence of ice easier, a second synchronous demodulator, 1107, is added, receiving its sinal input from low-pass filter, 1106, and with its synchronization input from control clock generator, 1101. The purpose of synchronous demodulator, 1107, is to level-shift the output of low-pass filter, 1106, by providing an output signal which alternates from zero, to the difference between the two output levels of low-pass filter, 1106. The output of synchronous demodulator, 1107, is low-pass filtered in low-pass filter, 1108, to provide a dc voltage with 5-Hz clock frequency ripple. The ripple amplitude versus response time of the system is a design tradeoff. A choice of cutoff frequency of low-pass filter, 1108, of 1.5 Hz would correspond to about three time constants, providing some smoothing of the 5 Hz ripple. The output of low-pass filter, 1108, is then compared with a reference voltage threshold level, Vth, provided by the output of voltage reference, 1110. Further ripple rejection may be provided by optionally following comparator, 1109, with a flip-flop, or by using a latching comparator for comparator 1109.

Some of the signals described above with respect to FIG. 11B are shown in FIG. 11C. The 5 Hz control clock is given as 1111. This controls dual frequency oscillator, 1102, to alternate between signal frequencies, f2, e.g., 200 Hz, 1112, and f3, e.g., 50 kHz, 1113. The output, 1115, of low-pass filter 1106, with ice, switches between high level, V2, 1116, and low level, V3, 1117, corresponding to 200 Hz and 50 kHz, respectively. The output of low-pass filter, 1108, is a dc level, with 5-Hz ripple, ideally of a value of (V2–V3), 1118. The value of (V2–V3) may be "processed" by comparison with a minimum threshold level required to indicate presence of ice.

In the absence of ice, as explained above, liquid-state water has a dielectric constant of about 80, which is substantially constant with frequency. Thus, the outputs, 1119 and 1120, of low-pass filters, 1106 and 1108, respectively, are substantially zero volts in the absence of ice.

Figure 12:
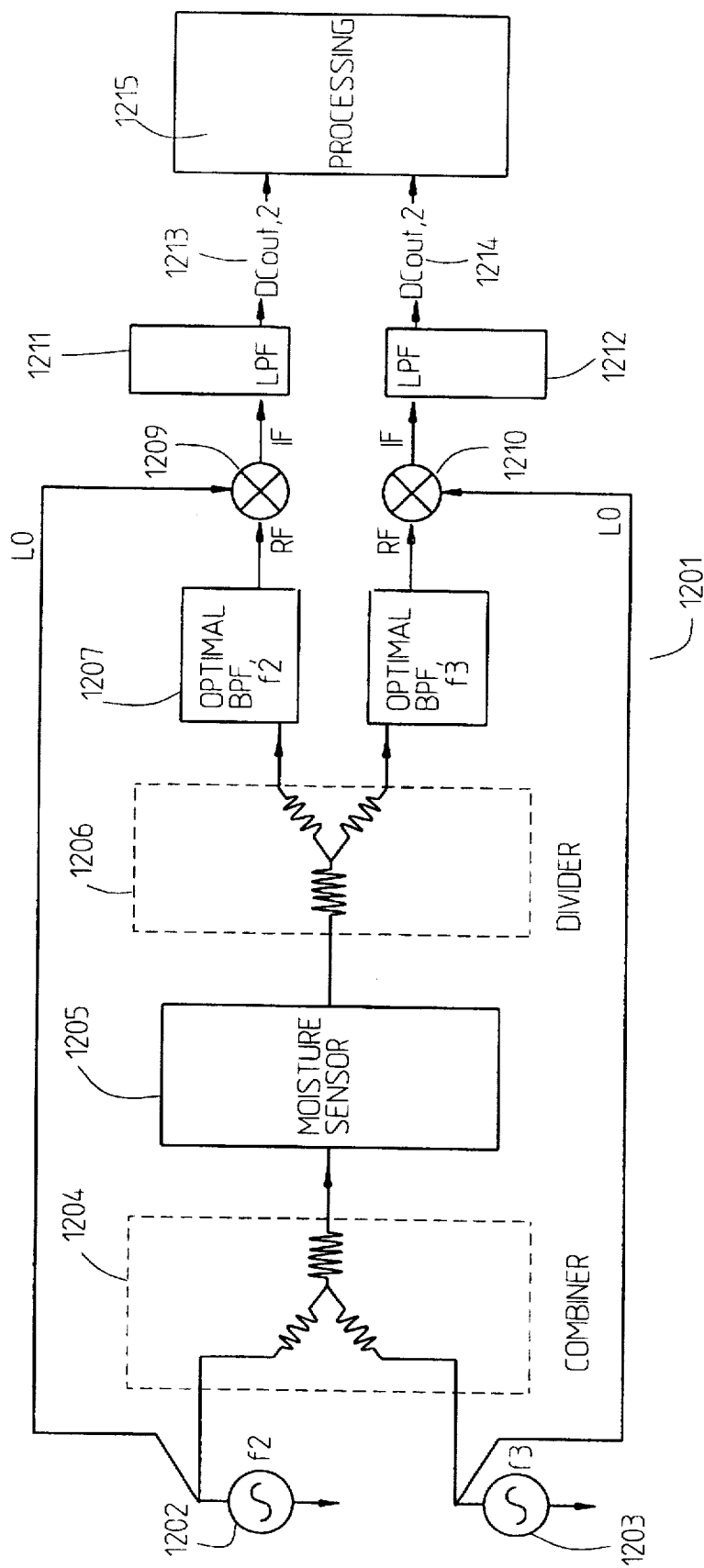
FIG. 12 is a block diagram an alternative ice sensor realization.

An alternate ice sensor electronics realization is shown in FIG. 12. Here two oscillators operate continually, continuously providing their respective DC outputs to a decision-making processor block which may compare the DC output levels, or take the ratio of the DC output levels to measure the ratio of the dielectric constants at the two frequencies, for the case that the oscillator output levels are either equal, or of a known ratio, which information is provided to the "processor". The processor may include voltage comparators and ratio circuits as are well known analogue methods of providing an output indication from DC levels such as will be available here. Ice detection system, 1201, includes oscillators, 1202 and 1203, operating at frequencies f2 and f3, respectively. The oscillator outputs are combined in combiner, 1204, and applied to moisture sensor, 1205. The output of moisture sensor, 1205, is divided in divider, 1206, the outputs of which are optionally band-pass filtered in band-pass filters, 1207 and 1208, before being applied to "RF" inputs of mixers, 1209 and 1210, respectively. The "LO" inputs of mixers, 1209 and 1210, are provided by oscillators 1202 and 1203, thereby providing synchronous demodulation of the input signals to the mixers. The "IF" outputs of the mixers are low-pass filtered in low-pass filters, 1211 and 1212, to provide DC level outputs, 1213 and 1214, respectively, to processor, 1215. The simplest possible processor, 1215, would include two reference voltages for two voltage comparators, for determining whether the DC output level, 1213, corresponding to lower excitation frequency, f2, exceeds a minimum threshold level, while the DC output level, 1214, corresponding to greater excitation frequency, f3, remains below a maximum level. This would provide detection of moisture at f2 based on level 1213, and would indicate that the detected moisture is not liquid-phase water at f3 based on level 1214.

The ice detector of the present invention has many beneficial applications, in addition to automatically clearing snow from windshields. Another application is as an "icing" detector for airplanes. A sensor panel may be fitted to the airplane wings, for example, for "icing detection", providing a warning to the pilot. Similarly, the ice detector may be employed as an automotive "freezing-rain" detector, providing a warning indication to the automobile driver, of the rapidly-developing hazardous driving condition he is in.

A further variation on this theme, is a remote telemetry system, for highway weather monitoring, for example on the interstate highways. Weather-monitoring installations which include the differential moisture detector of the present invention for moisture detection, and which also include the ice detector of the present invention, can transmit weather status to state police dispatchers for example, who may warn the patrol cars of dangerous driving conditions, and who may also provide the additional weather and driving conditions information for posting at highway toll booths.

Figure 11D:
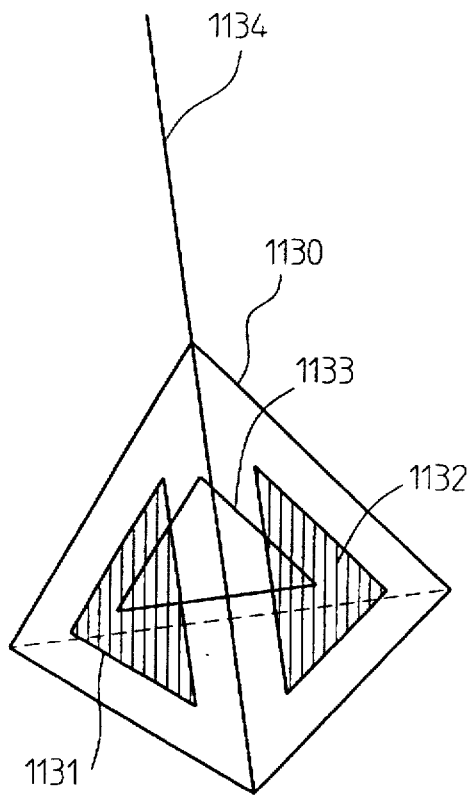
FIG. 11D illustrates a remote-weather sensing package.

A suitable remote monitoring device might have a configuration as shown in FIG. 11D. With sensors located in areas 1131, 1132, and 1133, of pyramid, 1130, precipitation arriving from above or from any of the four directions must certainly intercept at least one face of the Figure. The sensor connections may be parallelled and connected to electronics contained inside the shape, which may serve as a weather-proof housing. The housing could optionally contain a transmitter, with an optional antenna, 1134, mounted on the top of the pyramid. The sensors and electronics would then have to be designed and tested to be insensitive to the transmissions.

As a further construction detail, it will be appreciated that the moisture detectors of the present invention may be constructed in a two-sided manner, with the two sensors back-to-back, having a common shield plate between the sensors. Each sensor would be on a first surface of a substrate. The second surfaces of the two substrates would be placed together, with the shared, common shield plate between the two second surfaces. Thus the two sensors could occupy the same windshield area. This would represent a cost-savings in substrate material, and allow smaller-sized dual-sensors.

Further, a typical material for making a transparent conductive coating is 3,44 Ethylene Dioxy Thiophene (EDT) made by Bayer.

While the invention has been described with respect to a limited number of embodiments, it will be appreciated that many variations, modifications, and other applications of the invention may be made.

For example, the moisture detector of the invention may be implemented as a stand-alone device, not integrally simultaneously fabricated with the automotive windshield, but which can be mounted to an existing windshield. In this case, it is not necessary to use the laminated "sandwich" glass substrate, but deposition of electrodes on the two sides of a flexible plastic sheet substrate would be sufficient, in which case this device would then be adhered onto the windshield, and wires would connect to the electronics package. A sandwich glass-substrate could also be made, but would usually require glass substrate with matching curvature to that of the windshield it was to be mounted on.

Additionally, further benefit may result from interconnection of a multiplicity of moisture sensors which sense regions of the same surface, to provide a resulting overall moisture sensor which is still less sensitive to substrate changes than one sensor alone.

For the purpose of the claims, "moisture" shall be understood to include water in any phase.

It is clear from the above disclosure that depending on the excitation and detection electronics the same sensor may be used to detect water in different physical phases of water.

As discussed above with respect to FIG. 10C, the capacitance of a parallel-plate capacitor is ideally proportional to A/d, where A is the area of the capacitor plate, and d is the distance between the two plates of the capacitor. However, it is important to realize that this depends on the capacitance contribution due to fringing field effects at the edges of the capacitor plates being insignificant compared with the capacitance "inside" the capacitor plate area. For the capacitor realization of the present invention, the capacitor plates are clearly "long, narrow" plates, having very little "inside" area. Thus, fringing field effects are expected to be significant. The capacitance will still be related to A/d, but will not be strictly proportional. So we may speak of a capacitor with an "effective A/d" ratio. And for two capacitances with a common dielectric, but with different values of A and d, to be equal, the two capacitors must have equal "effective A/d" ratios. Thus, in the claims, the use of "effective ratios of A/d". Further, it will be appreciated that even with identical photomask patterns, two devices can not be expected to match perfectly. Hence, the use of "substantially equal", rather than "equal", in claim 1.

What is claimed is:

1. A fringing-field differential capacitive moisture sensor, comprising (a) first and second fringing-field capacitances formed between first and second pairs of capacitive electrode plates, respectively, said pairs of capacitive electrode plates having first and second pairs of values of A, effective capacitive plate area, and d, effective capacitive separation distance between the two plates of each said pair of capacitive electrode plates, respectively, said fringing-field capacitances having first and second effective ratios of A/d, respectively, said first and second effective ratios of A/d of said first and second fringing-field capacitances being substantially equal, whereby said first and second fringing-field capacitances having substantially equal values of capacitance; and, (b) a dielectric having a dielectric thickness and first and second surfaces, said first and second pairs of capacitive electrode plates in contact with said first surface of said dielectric, said first and second pairs of capacitive electrode plates having first and second ratios of effective capacitive separation distance, d, to dielectric thickness, respectively;

said first ratio of effective separation distance, d, to dielectric thickness sufficiently large that the fringing field of said first fringing-field capacitor extends beyond said second surface of said dielectric, said second ratio of effective separation distance to dielectric thickness sufficiently small that the fringing field of said second fringing-field capacitor is substantially totally contained within said dielectric, whereby, the fringing-field differential capacitive moisture sensor having substantially equal dry first and second fringing-field capacitances, resulting in a substantially zero dry-condition sensor output signal, thereby providing insensitivity of a resulting sensor wet-condition output signal to variations in said dielectric versus temperature and stress.

2. A fringing-field differential capacitive moisture sensor as in claim 1, wherein said first pair of capacitive electrode plates have said first value of d comparable to said dielectric thickness; and said second pair of capacitive electrode plates have said second value of d smaller than said dielectric thickness.

3. A fringing-field differential capacitive moisture sensor as in claim 1, further comprising (a) a second dielectric; and, (b) a shield electrode located in a plane parallel to said capacitive electrode plates and said second dielectric, said capacitive electrode plates separated by said second dielectric from said shield electrode.

4. A fringing-field differential capacitive moisture sensor as in claim 1, further comprising (a) a flexible substrate;

(b) said capacitive electrode plates fabricated on said substrate; and, (c) said substrate having an extension serving as a ribbon cable.

5. A fringing-field differential capacitive moisture sensor assembly for sensing moisture on a second surface of a glass window having first and second surfaces, comprising:

(a) a first plastic laminate having first and second surfaces;

(b) at least three non-reference active plates on said first surface of said first plastic laminate;

(c) a shield electrode on said second surface of said first plastic laminate, said shield electrode serving to provide directionality, said sensor assembly placed against the first surface of the glass window, with said first surface of said first plastic laminate toward the first surface of the glass window;

said at least three non-reference active plates on said first surface of said first plastic laminate providing first and second pairs of capacitive electrode plates, (a) first and second fringing-field capacitances formed between said first and second pairs of capacitive electrode plates, respectively, said pairs of capacitive electrode plates having first and second pairs of values of A, effective capacitive plate area, and d, effective capacitive separation distance between the two plates of each said pair of capacitive electrode plates, respectively, said fringing-field capacitances having first and second effective ratios of A/d, respectively, said first and second effective ratios of A/d of said first and second fringing-field capacitances being substantially equal, whereby said first and second fringing-field capacitances having substantially equal values of capacitance; and, (b) the glass window being a dielectric having a dielectric thickness and first and second surfaces, said first and second pairs of capacitive electrode plates in contact with said first surface of said dielectric, said first and second pairs of capacitive electrode plates having first and second ratios of effective capacitive separation distance, d, to dielectric thickness, respectively;

said first ratio of effective separation distance, d, to dielectric thickness sufficiently large that the fringing field of said first fringing-field capacitor extends beyond said second surface of said dielectric, said second ratio of effective separation distance to dielectric thickness sufficiently small that the fringing field of said second fringing-field capacitor is substantially totally contained within said dielectric, whereby, the fringing-field differential capacitive moisture sensor having substantially equal dry first and second fringing-field capacitances, resulting in a substantially zero dry-condition sensor output signal, thereby providing insensitivity of a resulting sensor wet-condition output signal to variations in said dielectric versus temperature and stress.

6. A fringing-field differential capacitive moisture sensor assembly as in claim 5, said glass window further comprising first and second glass laminates, each said first and second glass laminate being first and second dielectrics, respectively, and having a first surface and a second surface, said first surfaces of said first and second glass laminates oriented toward each other, said first plastic laminate sandwiched between said first glass laminate and said second glass laminate, (a) said sensor assembly placed against said first surface of said first glass laminate, (b) said first surface of said first plastic laminate toward said first surface of said first glass laminate.

7. A fringing-field differential capacitive moisture sensor assembly as in claim 6, further comprising (a) a second plastic laminate having first and second surfaces, (b) at least three non-reference active plates on said first surface of said second plastic laminate; and (c) a shield electrode on said second surface of said second plastic laminate, said shield electrode serving to provide directionality;

said first plastic laminate and said second plastic laminate sandwiched between said first glass laminate and said second glass laminate, said first surface of said first plastic laminate toward said first surface of a said first glass laminate, and said first surface of said second plastic laminate coward said first surface of said second glass laminate;

said at least three non-reference active plates on said first surface of said second plastic laminate providing third and fourth pairs of capacitive electrode plates, thereby providing a second fringing-field moisture sensor, including (a) third and fourth fringing-field capacitances formed between said third and fourth pairs of capacitive electrode plates, respectively, said pairs of capacitive electrode plates having third and fourth pairs of values of A, effective capacitive plate area, and d, effective capacitive separation distance between the two plates of each said pair of capacitive electrode plates, respectively, said fringing-field capacitances having third and fourth effective ratios of A/d, respectively, said third and fourth effective ratios of A/d of said third and fourth fringing-field capacitances being substantially equal, whereby said third and fourth fringing-field capacitances having substantially equal values of capacitance; and, (b) said second glass laminate being said second dielectric having a dielectric thickness and first and second surfaces, said third and fourth pairs of capacitive electrode plates in contact with said first surface of said second dielectric, said third and fourth pairs of capacitive electrode plates having third and fourth ratios of effective capacitive separation distance, d, to second dielectric thickness, respectively;

said third ratio of effective separation distance, d, to dielectric thickness sufficiently large that the fringing field of said third fringing-field capacitor extends beyond said second surface of said second dielectric, said fourth ratio of effective separation distance to dielectric thickness sufficiently small that the fringing field of said fourth fringing-field capacitor is substantially totally contained within said second dielectric, whereby, said second fringing-field differential capacitive moisture sensor having substantially equal dry third and fourth fringing-field capacitances, resulting in a substantially zero dry-condition second sensor output signal, thereby providing insensitivity of a resulting second sensor wet-condition output signal to variations in said second dielectric versus temperature and stress.

8. A fringing-field differential capacitive moisture sensor assembly as in claim 7, wherein said second surfaces of said first and said second plastic laminates oriented toward each other, said second surfaces of said first and second plastic laminates sharing a common shield electrode common to said second sides of said first and second plastic laminates, thereby acting as a shield between said non-reference active plates of said first and second plastic laminates.

9. A method for detecting presence of ice on a second surface of a dielectric, the dielectric having first and second surfaces, comprising
(a) providing a fringing-field capacitive moisture sensor including
(1) first and second fringing-field capacitances formed between first and second pairs of capacitive electrode plates, respectively, said pairs of capacitive electrode plates having first and second pairs of values of A, effective capacitive plate area, and d, effective capacitive separation distance between the two plates of each said pair of capacitive electrode plates, respectively, said fringing-field capacitances having first and second effective ratios of A/d, respectively, said first and second effective ratios of A/d of said first and second fringing-field capacitances being substantially equal, whereby said first and second fringing-field capacitances having substantially equal values of capacitance; and,
(2) a dielectric having a dielectric thickness and first and second surfaces,
said first and second pairs of capacitive electrode plates in contact with said first surface of said dielectric,
said first and second pairs of capacitive electrode plates having first and second ratios of effective capacitive separation distance, d, to dielectric thickness, respectively,
said first ratio of effective separation distance, d, to dielectric thickness sufficiently large that the fringing field of said first fringing-field capacitor extends beyond said second surface of said dielectric,
said second ratio of effective separation distance to dielectric thickness sufficiently small that the fringing field of said second fringing-field capacitor is substantially totally contained within said dielectric,
whereby, the fringing-field differential capacitive moisture sensor having substantially equal dry first and second fringing-field capacitances, resulting in a substantially zero dry-condition sensor output signal, thereby providing insensitivity of a resulting sensor wet-condition output signal to variations in said dielectric versus temperature and stress;
(b) exciting said moisture sensor alternately with alternating current of at least two frequencies
(c) detecting resulting alternating current signal output of said capacitive moisture sensor at each said frequency, said detecting of each said alternating current signal output of said capacitive moisture sensor at each of said least two frequencies resulting in DC outputs corresponding to the signal coupling through said sensor at each said frequency; and,
(d) processing said DC outputs to determine whether ice is present on the first surface of the dielectric.

10. A device for detecting presence of ice on a second surface of a dielectric having first and second surfaces, comprising
(1) a fringing-field capacitive moisture sensor including
(a) first and second fringing-field capacitances formed between first and second pairs of capacitive electrode plates, respectively, said pairs of capacitive electrode plates having first and second pairs of values of A, effective capacitive plate area, and d, effective capacitive separation distance between the two plates of each said pair of capacitive electrode plates, respectively, said fringing-field capacitances having first and second effective ratios of A/d, respectively, said first and second effective ratios of A/d of said first and second fringing-field capacitances being substantially equal, whereby said first and second fringing-field capacitances having substantially equal values of capacitance; and,
(b) a dielectric having a dielectric thickness and first and second surfaces,
said first and second pairs of capacitive electrode plates in contact with said first surface of said dielectric,
said first and second pairs of capacitive electrode plates having first and second ratios of effective capacitive separation distance, d, to dielectric thickness, respectively;
said first ratio of effective separation distance, d, to dielectric thickness sufficiently large that the fringing field of said first fringing-field capacitor extends beyond said second surface of said dielectric,
said second ratio of effective separation distance to dielectric thickness sufficiently small that the fringing field of said second fringing-field capacitor is substantially totally contained within said dielectric,
whereby, the fringing-field differential capacitive moisture sensor having substantially equal dry first and second fringing-field capacitances, resulting in a substantially zero dry-condition sensor output signal, thereby providing insensitivity of a resulting sensor wet-condition output signal to variations in said dielectric versus temperature and stress; and,
(2) instrumentation including,
(a) a dual-frequency oscillator for providing two output frequencies for excitation of said moisture sensor;
(b) a clock oscillator providing a low-frequency clock output, for control of said dual-frequency oscillator;
(c) a first mixer for synchronously detecting said moisture output signal at each said output frequency, providing an alternating, single-polarity, two-level, first mixer output signal;
(d) a second mixer for synchronously detecting said first mixer output signal with respect to said low-frequency clock output, thereby transforming said first mixer output signal to a substantially DC, ground-referenced, second mixer output signal; and,
(e) a processor for determining whether ice is present, based on said DC outputs corresponding to each said moisture output signal at each said excitation frequency.

11. A device for detecting presence of ice on a second surface of a dielectric having first and second surfaces, comprising
(a) a fringing-field capacitive moisture sensor including
(1) first and second fringing-field capacitances formed between first and second pairs of capacitive electrode plates, respectively, said pairs of capacitive electrode plates having first and second pairs of values of A, effective capacitive plate area, and d, effective capacitive separation distance between the two plates of each said pair of capacitive electrode plates, respectively, said fringing-field capacitances having first and second effective ratios of A/d, respectively, said first and second effective ratios of A/d of said first and second fringing-field capacitances being substantially equal, whereby said first and second fringing-field capacitances having substantially equal values of capacitance; and, (2) a dielectric having a dielectric thickness and first and second surfaces, said first and second pairs of capacitive electrode plates in contact with said first surface of said dielectric, said first and second pairs of capacitive electrode plates having first and second ratios of effective capacitive separation distance, d, to dielectric thickness, respectively;

said first ratio of effective separation distance, d, to dielectric thickness sufficiently large that the fringing field of said first fringing-field capacitor extends beyond said second surface of said dielectric, said second ratio of effective separation distance to dielectric thickness sufficiently small that the fringing field of said second fringing-field capacitor is substantially totally contained with said dielectric, whereby, the fringing-field differential capacitive moisture sensor having substantially equal dry first and second fringing-field capacitances, resulting in a substantially zero dry-condition sensor output signal, thereby providing insensitivity of a resulting sensor wet-condition output signal to variations in said dielectric versus temperature and stress;

said fringing-field differential capacitive moisture sensor for excitation by at least two excitation frequencies, said fringing-field differential capacitive moisture sensor for providing a moisture output signal at each said excitation frequency;

(b) at least two oscillators for providing respectively at least two said excitation frequencies for excitation of said moisture sensor;

(c) at least two mixers for synchronously detecting each said moisture output signal at each said excitation frequency, each said mixer for providing a DC output corresponding to each said moisture output signal at each said excitation frequency; and, (d) a processor for determining whether ice is present, based on said DC outputs corresponding to each said moisture output signal at each said excitation frequency.

12. A fringing-field differential capacitive moisture sensor as in claim 1, wherein said capacitive electrode plates are fabricated by deposition of a substantially transparent conductive thin film on a substrate.

* * * * *